(12) United States Patent
Andrews

(10) Patent No.: US 11,324,638 B2
(45) Date of Patent: May 10, 2022

(54) BANDAGE WHICH ENABLES EXAMINING OR TREATING A WOUND WITHOUT REMOVING THE ADHESIVE

(71) Applicant: Peter B Andrews, Indianan Township, PA (US)

(72) Inventor: Peter B Andrews, Indianan Township, PA (US)

( * ) Notice: Subject to any disclaimer, the term of this patent is extended or adjusted under 35 U.S.C. 154(b) by 0 days.

(21) Appl. No.: 17/303,430

(22) Filed: May 28, 2021

(65) Prior Publication Data
US 2021/0282975 A1  Sep. 16, 2021

(51) Int. Cl.
*A61F 13/00*  (2006.01)
*A61F 13/02*  (2006.01)

(52) U.S. Cl.
CPC .......... *A61F 13/00* (2013.01); *A61F 13/0266* (2013.01); *A61F 2013/0057* (2013.01)

(58) Field of Classification Search
CPC ....... A61M 225/0253; A61M 225/0266; A61F 13/00; A61F 13/0266; A61F 13/0246; A61F 2013/0027; A61F 2013/00089; A61F 2013/024; A61F 2013/00553; A61F 2013/0057; A61F 2013/0233; A61F 2013/00565
USPC .......................... 604/180, 192; 128/888, 889
See application file for complete search history.

(56) References Cited

U.S. PATENT DOCUMENTS

| | | | |
|---|---|---|---|
| 4,263,906 A | | 4/1981 | Finley |
| 4,641,643 A * | | 2/1987 | Greer ................. A61F 13/0246 128/888 |
| 5,072,738 A * | | 12/1991 | Wonder ................ A61F 15/008 128/888 |
| 5,086,763 A * | | 2/1992 | Hathman ............ A61F 13/0246 128/887 |
| 5,702,356 A * | | 12/1997 | Hathman ............ A61F 13/0206 128/888 |
| 5,961,480 A | | 10/1999 | Augustine |
| 6,005,159 A * | | 12/1999 | Spier ...................... A61F 15/004 128/888 |
| 6,247,787 B1 | | 8/2001 | Downing |
| 2007/0282236 A1* | | 12/2007 | LaGreca ............ A61F 13/0206 602/43 |
| 2012/0197206 A1* | | 8/2012 | Glenn .................... A61M 25/02 604/180 |
| 2019/0117939 A1* | | 4/2019 | Price ..................... A61M 25/02 |

(Continued)

*Primary Examiner* — Kim M Lewis
(74) *Attorney, Agent, or Firm* — Lawrence S. Pope

(57) ABSTRACT

The base of this bandaging system is attached to the skin around a wound by adhesive and supports the edges of the lid, which covers the wound and can easily be removed and replaced or re-used many times to facilitate examining or treating the wound while the base remains in place. The bandaging system has multiple embodiments to accommodate various situations. An embodiment with generally planar components is very simple but may cause vertical pressure on the skin near the wound when the lid is removed or attached. Such pressure is avoided by alternative embodiments in which the components have non-planar parts. Some embodiments have a hinge on an edge of the lid which allows the wound to be uncovered without detaching the lid. The components which latch lids to bases contribute to making the systems easy, quick, convenient, and comfortable to use.

15 Claims, 16 Drawing Sheets

(56) References Cited

U.S. PATENT DOCUMENTS

2020/0282182 A1\* 9/2020 Blackman ............ A61M 25/02
2021/0100690 A1 4/2021 Levy et al.

\* cited by examiner

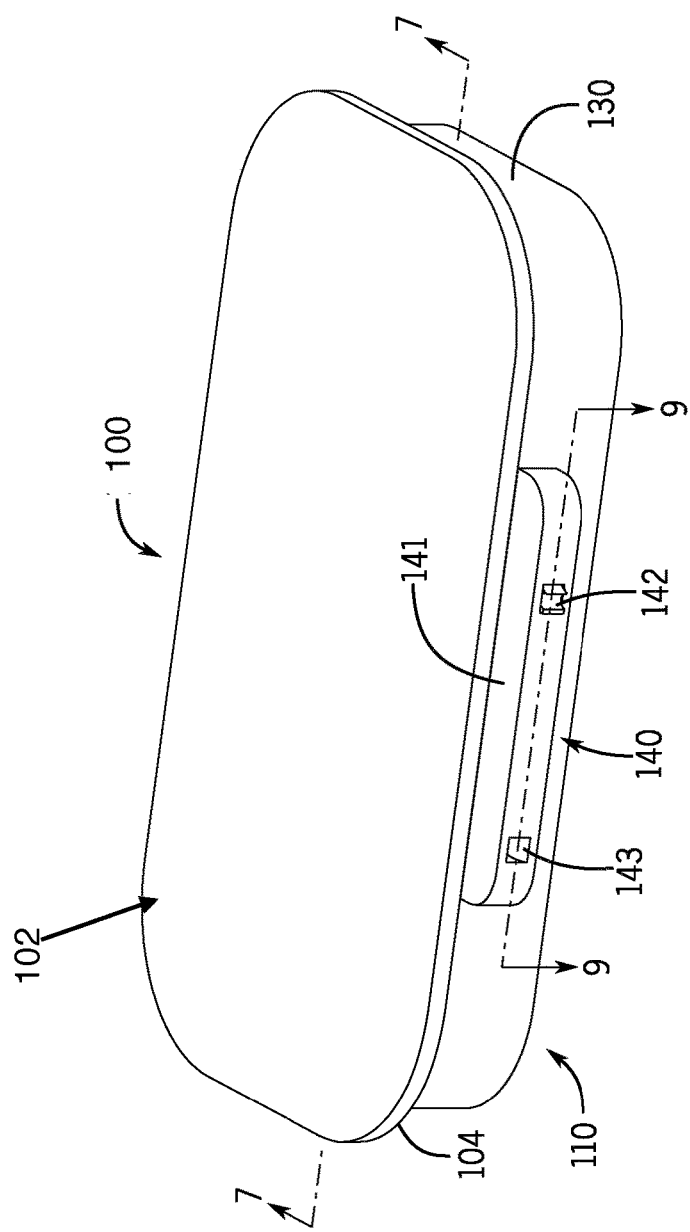
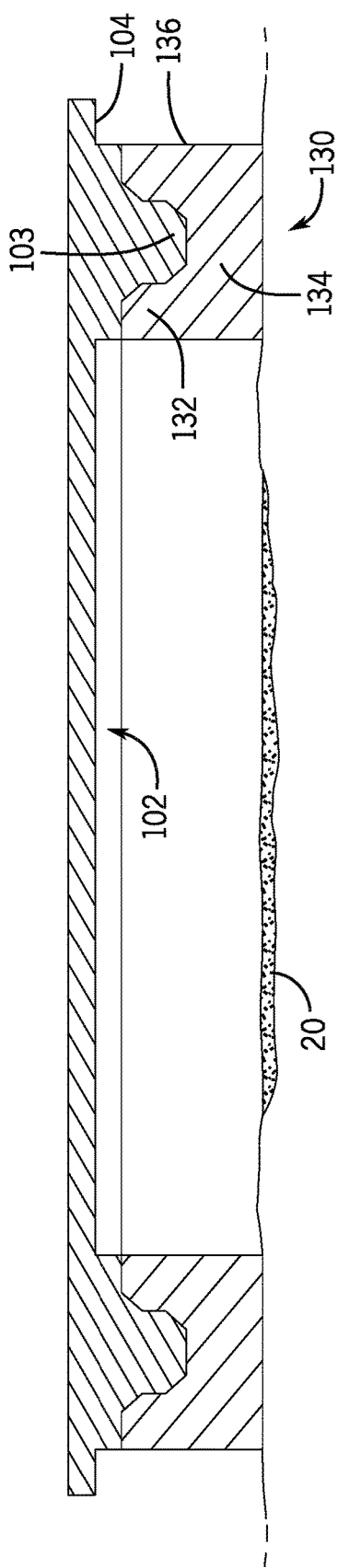
FIG. 6
FIG. 7

BANDAGE WHICH ENABLES EXAMINING OR TREATING A WOUND WITHOUT REMOVING THE ADHESIVE

BACKGROUND OF THE INVENTION

We shall refer to what a bandage covers as a wound, though it might also be called a cut, scratch, scrape, burn, blister, sore, traumatic insult or blemish. It is often necessary to examine, clean, medicate, or treat a bandaged wound many times. This requires removing the bandage, and later bandaging the wound again. This takes time from those who do it, who may be health professionals or other persons who are very busy or whose time is very valuable. It may also be inconvenient or uncomfortable for the patient who has the wound. Sometimes many bandages are eventually used for one wound. We say that a wound is needy if it needs to be examined or treated more than once before it is healed.

BRIEF SUMMARY OF THE INVENTION

The present invention involves a multicomponent bandaging system to address a wound in human skin and allows repeated ready access to the wound without repeated application and removal of a bandage from the skin surrounding the wound. It has a base that defines a boundary around an aperture of a size sufficient to encompass a wound or other affliction of human skin that merits repeated attention during its healing. It has a generally planar portion adapted to adhere to human skin such that it is not easily dislodged and yet can be removed without causing significant pain and it has a portion adapted to repeatedly engage with and be disengaged from a lid without adversely affecting the adherence of the base to human skin. The bandaging system also has a generally planar lid that is adapted to substantially cover the base. The lid also has a portion adapted to repeatedly engage with and be disengaged from the base. The base may be provided with a suitable adhesive prior to or at the time of its application to the human skin. In the former case it may be provided with a protective readily removable cover sheet.

In some embodiments the base and the lid each have a portion that interacts with a portion of the other that does not lie in a plane generally parallel to the portion of human skin to which the base is to adhere. These portions are adapted to interact such that the lid can be detached from base without causing any significant stress to the skin surrounding the wound or other affliction of human skin.

BRIEF DESCRIPTION OF THE SEVERAL VIEWS OF THE DRAWINGS

FIG. 6 is a perspective view of an embodiment of the bandaging system with the base having an upstanding wall and a locking assembly.

FIG. 7 is a cross section of FIG. 6 along line 7-7.

DETAILED DESCRIPTION OF THE INVENTION

Overview of the Banj Bandaging System

Figure 1:
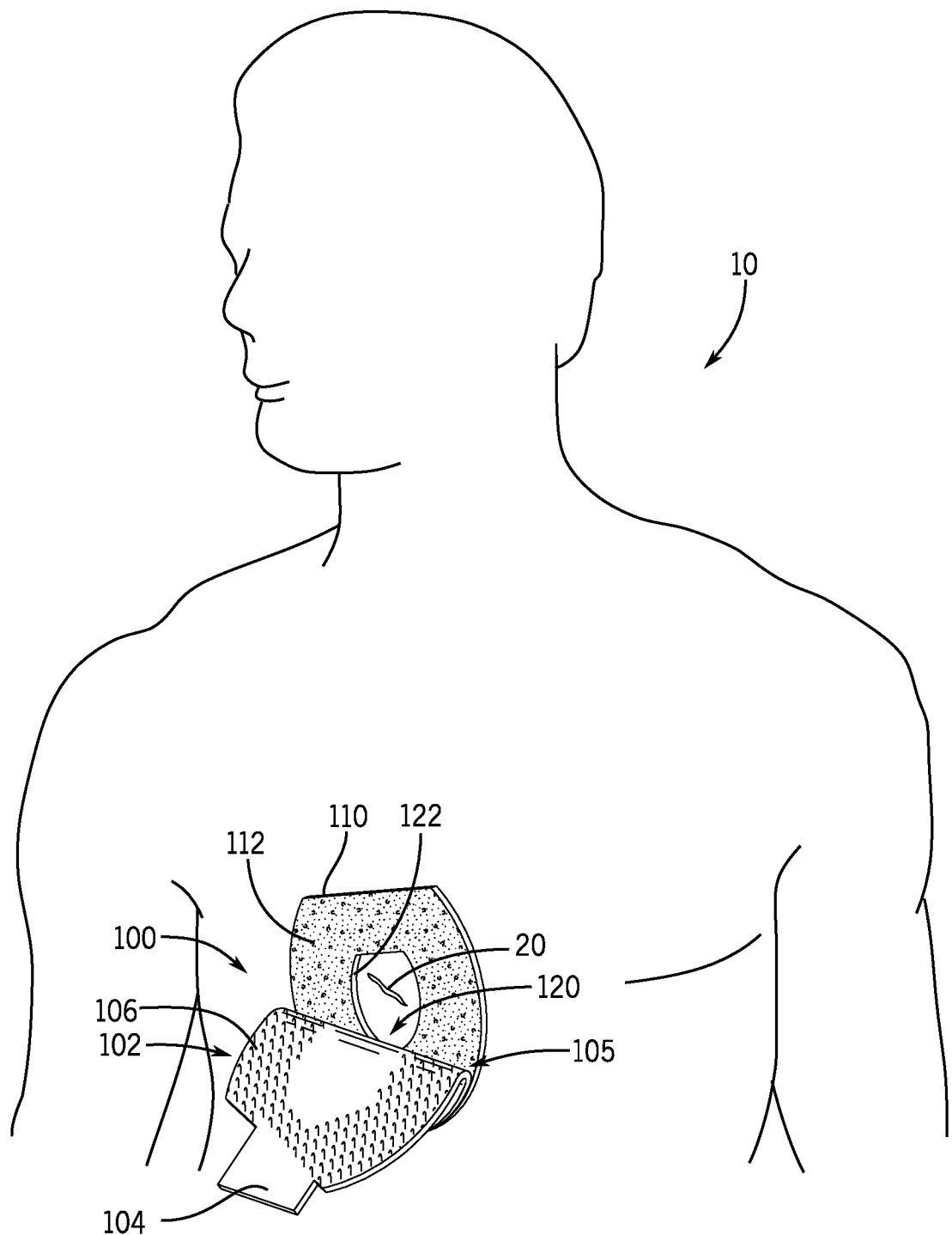
FIG. 1 is a perspective view of a human patient with wound which is addressed by a Banj Simple bandaging system.

A Banj bandaging system is an enhanced bandage which is better than an ordinary bandage for bandaging needy wounds. Except in cases where something like an Ace bandage is used to hold the wound-covering in place, removing a traditional bandage involves removing the adhesive portion which holds the bandage in place. One can think of a Banj bandaging system as a bandage which permits the adhesive to remain in place while the wound-covering is temporarily removed.

We shall say that a bandage is persistent if it permits one to uncover the wound and then cover it again without entirely removing and replacing the bandage. A persistent bandage is most appropriate for a needy wound. A Banj bandaging system is a persistent bandage.

We shall refer to anyone who deals with a wound or a bandage for it as a caregiver. We shall write 'e as an abbreviation for he or she, and 'e's as an abbreviation for his or her or hers.

Basic Features and Their Advantages

A Banj bandaging system has two components, which we call the base and the lid. The lid covers the wound, and its edges rest upon the base. The base is designed so that it can be used for as long as the wound needs to be covered, while the lid can easily be removed and then put on again or replaced by a new lid.

There are a number of advantages for using a Banj bandaging system when the wound is needy. There is less potential irritation of the patient's skin. The wound can be uncovered and covered again very quickly and easily. This benefits both the caregiver and the patient. Sometimes a patient with no immediate access to a caregiver gets worried that e's wound is getting infected or having some other problem. With a Banj bandaging system covering the wound, in many cases such a patient can easily uncover the wound, examine it, and cover it again without the help of a caregiver.

Since the wound is visible inside the base when the base is being put on, it is very easy to initially place the Banj bandaging system in exactly the right place. It may be more economical to use one Banj bandaging system, perhaps with extra lids, than to use many bandages.

Banj bandaging systems are designed to avoid or minimize sharp edges and protruding structures which might cause scratches or other problems. It is advantageous for the corners to be rounded.

A Banj bandaging system may be somewhat more bulky than a traditional bandage, but that may not matter when the wound is sufficiently serious that it requires continuing attention. Even if in some cases a Banj bandaging system costs more than traditional bandages, it is likely that savings in the valuable time of expensive caregivers will more than compensate for this.

Banj Bandaging Systems Have a Variety of Forms

Just as there are many types of bandages, there are many types of Banj bandaging systems, differing from one another in size, shape, and certain features. There is a family of Banj bandaging systems, each designed to meet particular needs.

At least some Banj bandaging systems will be waterproof. Naturally, this necessitates a watertight seal between the base and the lid.

The lids, or portions of them, may be transparent in some Banj bandaging systems.

Some Banj bandaging systems provide ideal protection for wounds which need exposure to air. In this regard the lids of such systems can be fabricated from air permeable materials and/or be provided with pores of appropriate size to promote air flow.

Lids come in two forms, which we shall call plain and loaded. When using a Banj bandaging system with a plain lid, the caregiver may cover the wound with a dressing such as a (possibly non-stick) gauze pad which is not part of the Banj bandaging system, and then install the lid on top of this so that the lid holds it in place. A loaded lid has a dressing attached to it, so the entire lid will be replaced when the dressing needs to be replaced. Some caregivers may feel that the added convenience and time saving justifies any additional cost of loaded lids.

Some methods of attaching Banj bandaging system lids to bases, or releasing them, may produce downward or upward pressure on a portion of the base. This may be undesirable or even unacceptable for some wounds.

Banj Bandaging Systems Have Many Uses

People may discover non-bandage applications for Banj bandaging systems. For example, in a crowded kitchen one might keep keys and rings in Banj bandaging systems attached to the undersides of shelves. Around Valentine's Day heart-shaped Banj Box bandaging systems (which we discuss below) specially designed for the occasion might be found in surprising places. Post-It Notes are used very widely; Banj bandaging systems can serve as Post-It Notes with physical content.

Very large Banj Box bandaging systems and Banj Kwik bandaging systems could be produced and serve as packaging for storing or transporting various goods. We shall refer to such Banj bandaging systems as package Banj bandaging systems to distinguish them from the bandage Banj bandaging systems which we have been discussing. The package Banj bandaging systems would be extremely easy, convenient, and quick to open and securely close many times.

Technical Details

We now discuss the technical details involved in the design of Banj bandaging systems. When discussing mental pictures to help in the descriptions of certain details, even though the patient could actually be in any position, we shall always imagine that the wound is under the Banj bandaging system, so if one component is "above" another, it is at a level which is farther from the wound.

General Features

The Base

Each Banj bandaging system has a boundary, which is an imaginary line on the patient's skin at the inner edge of the base. The region of the patient's skin, and corresponding parts of the base and the lid, which is bounded by the boundary will be called the wound region of the skin, base, or lid. The entire wound will be inside the wound region. However, it is not necessary that the wound be entirely surrounded by the base. In some cases there may be a gap in the base such that the portion of the base immediately adjacent to the wound region does not constitute a closed figure.

We will discuss various models of Banj bandaging systems below. The boundaries of Banj Kwik bandaging systems are always rectangular, but the boundaries of other models of Banj bandaging systems can have a great variety of shapes. Geometrically speaking, most of them will have wound regions which are convex and connected, but this is not essential.

Banj Simple bandaging systems can be shaped by a caregiver to fit a particular wound.

Banj Box bandaging systems are suitable for being produced by a system in which custom designed Banj Box bandaging systems are ordered by submitting a pattern for the wound region using a suitable technology, and the bandaging systems are delivered very promptly, or produced by a local 3-D printer.

The bottom of the base is coated with an adhesive which will be used to attach the base to the patient's skin, and which can provide firm adhesion for many days without damage to the skin. The adhesive may have a protective readily removable cover sheet. It may be wise to use a suitable adhesive remover when the base is eventually removed. Even hospitals often neglect to use adhesive remover when its use is appropriate, so a small vial of adhesive remover with something like an eye dropper should perhaps be included in every package of Banj bandaging systems.

The Setex® adhesive technology should be considered as an alternative to a traditional adhesive. Details are available at the website "nanogrip.com" of the developer nanoGrip Inc of Pittsburgh, Pa.

Of course, package Banj bandaging systems will generally not have adhesive at the base.

The Lid

To facilitate raising the lid, certain places on the edge of the lid, called grips, are designed so that one can grasp the lid there. Unless the Banj bandaging system is extremely large or has a a very irregular shape, it needs at most two grips. When there are two, it is desirable that the two grips be located opposite each other so that when one pulls up on both of them simultaneously, the forces on the lid are balanced, and it comes straight up without tilting.

Hinges

On some models of Banj, there is a portion of the lid which functions like a hinge and allows the lid to be tilted up to uncover the wound without entirely removing the lid. We shall refer to this portion of the lid as a hinge, although it does not look like a door hinge. The caregiver may use a hinge on one side of the lid to raise the opposite side of the lid, like opening a door, swings this over to a position behind the hinge, examines and treats the wound, and then moves the lid back over the wound to cover it.

If the lid is sufficiently flexible the hinge may simply be a line where the lid will be folded up. Otherwise, a hinge is formed by some method such as using flexible plastic that sustains repeated bending without fatigue failure where it is needed.

Across the lid from each hinge there is a grip.

Three Basic Models of Banj Bandaging Systems

There are three basic models of Banj bandaging systems, each with potential variations as suggested above. These models are called Banj Simple, Banj Box, and Banj Kwik. Banj Simple has a base and a lid which are mostly planar. When using Banj Simple, closing or opening the lid may exert undesirable downward or upward pressure on the wound. In such situations, one can use Banj Box or Banj Kwik, the bases and lids of which are not entirely planar. In these Banj systems, the edge of the lid has a depending wall which fits between inner and outer sections of an upstanding wall around the edge of the base.

Banj Simple Bandaging System

The Basic Design of Banj Simple Bandaging System

Banj Simple bandaging system may have a base made of something flexible like cloth, so it can be used even if the skin near the wound has features such as bumps or major wrinkles. The base covers the skin around the wound, which is suitably close to the wound, but is not inside the wound region. The outer edge of the lid is directly over the outer edge of the base, but the lid covers the entire region inside its outer edge, including the wound region.

Fasteners

The lid and the base are attached to, or consist of, materials which we shall call fasteners, and which can be repeatedly stuck together and then pulled apart without significantly changing the strength of the adhesion between them. The fastener for the base will be called the base fastener, and the fastener for the lid will be called the lid fastener. In contexts where certain fasteners have been chosen, we may speak of an enhanced fastener, which is a fastener of the same type such that the lid and base enhanced fasteners adhere to each other more strongly than the chosen lid and base fasteners adhere to each other.

The base fastener and features of it are designed to align perfectly with the lid fastener and its features, so in certain contexts it suffices to describe the lid fastener. Examples of fasteners are hook-and-loop fasteners, such as Velcro® fasteners. We shall refer to any material of this sort as velc; a Velcro® fastener is the prime example of velc. Other suitable fastener systems include Setex® fasteners; materials equipped to stick together using the groove and bead technology which is used in re-sealable sandwich bags made by Ziplock and other companies; and magnetic materials.

Hinges

Banj Simple bandaging systems which have no hinges can be manufactured, but each Banj Simple bandaging system which we shall discuss will have a hinge in its lid. The hinge is located on a straight line which is perpendicular to the centerline, which is the imaginary line passing through the centers of the grip and the wound region. The hinge is located so that the wound region lies between the hinge and the grip. The hinge is very close to a portion of the boundary and may include a portion of the boundary.

Enhanced Fasteners

When the fastener is velc or other suitable material, the lid fastener and the base fastener may each contain a strip of enhanced fastener. The center of the lid enhanced fastener strip lies along the centerline. The strip is on the side of the lid which is away from the grip, and it extends from the boundary of the wound to the outer edge of the lid.

When the fastener materials are bead and groove, a strip of bead runs around the lower side of the lid near the outside edge of the lid, and there is a matching strip of groove on the upper side of the base. However, this strip of bead has a gap in the two places where it crosses the hinge; the two gaps divide the bead into two sections. In the section of bead which is not near the grip, and in the corresponding section of groove in the base, enhanced bead and groove fasteners are used.

When helpful or appropriate, the locations of hinges and enhanced fasteners may be indicated by distinctive colors.

Raising the Lid

When the lid is pulled up at the grip of a Banj Simple bandaging system which has either type of fasteners, moderate force will allow the lid to remain stuck to the base where the enhanced fasteners are, so only the portion of the lid which is on the same side of the hinge as the wound region will come up. If the caregiver decides to remove the lid completely, 'e simply applies enough force to overcome the adhesion at the enhanced fasteners.

Rationale for Enhanced Fasteners

It would obviously be possible to produce somewhat simpler Banj Simple bandaging systems in which there are no enhanced fasteners. To uncover the wound while using such a bandaging system, a caregiver could simply remove the lid completely, or utilize a hinge by pulling up the lid very carefully and halting the process when the wound was uncovered but the lid was not yet entirely detached. The design philosophy for Banj bandaging systems is that things should be made as simple as possible for the caregiver, so that 'e can concentrate on caring for the wound and pay very little attention to the Banj bandaging system. The enhanced fasteners help achieve this objective.

FIG. 1 is an illustration of a human patient 10 who has a wound 20 that is being addressed with a bandaging system 100. The bandaging system 100 is composed of a lid 102 and a base 110. The lid 102 has a grip 104 and carries a hook and loop fastener 106 such as a Velcro® fastener on one surface. The base 110 has a wound region 120 that in turn has a perimeter called the boundary 122 that encompasses the wound 20 and its own hook and loop fastener 112. The bandaging system 100 facilitates repeated access to the wound 20 without having to rebandage it. Initially the wound 20 is encompassed by the base 110, and the base 110 is covered by the lid 102. Appropriate dressings or medicaments may be sandwiched between the lid 102 and the wound 20. To access the wound for inspection or appropriate treatment the lid 102 is grasped by its grip 104 and partially separated from the base 110 by bending it at the hinge 105 to allow free access to the wound 20. Subsequently the lid 102 can be secured to the base 110 by the action of the lid hook and loop fastener 106 and the base hook and loop fastener 112 in such a way that the base aperture 120 and the wound 20 are covered by the lid 102. The two hook and loop fasteners 106 and 112 facilitate repeated access to the wound 20 without affecting the bond of the base 110 to the skin of human patient 10.

Figure 2:
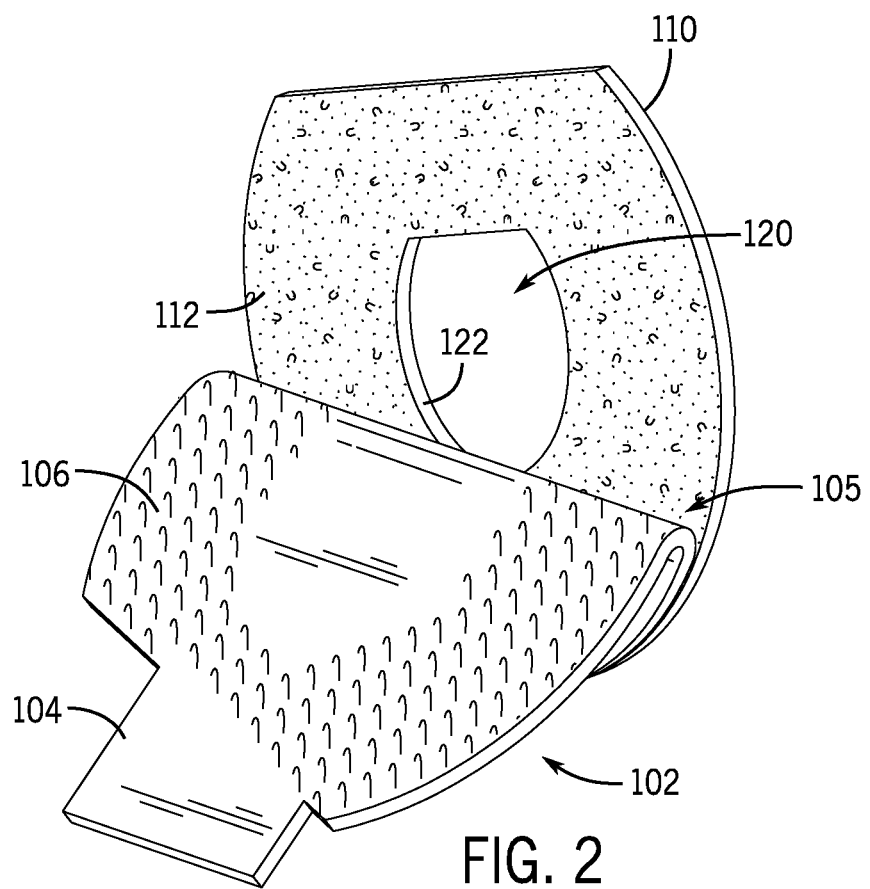
FIG. 2 is a perspective view of the bandaging system shown on the human in FIG. 1.

FIG. 2 provides a perspective view of just the bandaging system 100, shown on the human in FIG. 1. The lid 102 is adhered to the base 110. The lid 102 has a hook and loop fastener 106. The base 110 has a hook and loop fastener 112 and a wound region 120 with a boundary 122 that is adapted to surround a wound 20 (shown in FIG. 1). The flexibility of the lid 102 at the hinge 105 enables it to be closed and opened with a hinging mode of operation. The lid 102 has a grip 104 which can be used to grasp the lid 102 when the bandaging system is closed and needs to be opened so that the wound 20 can be examined or treated.

Figure 3:
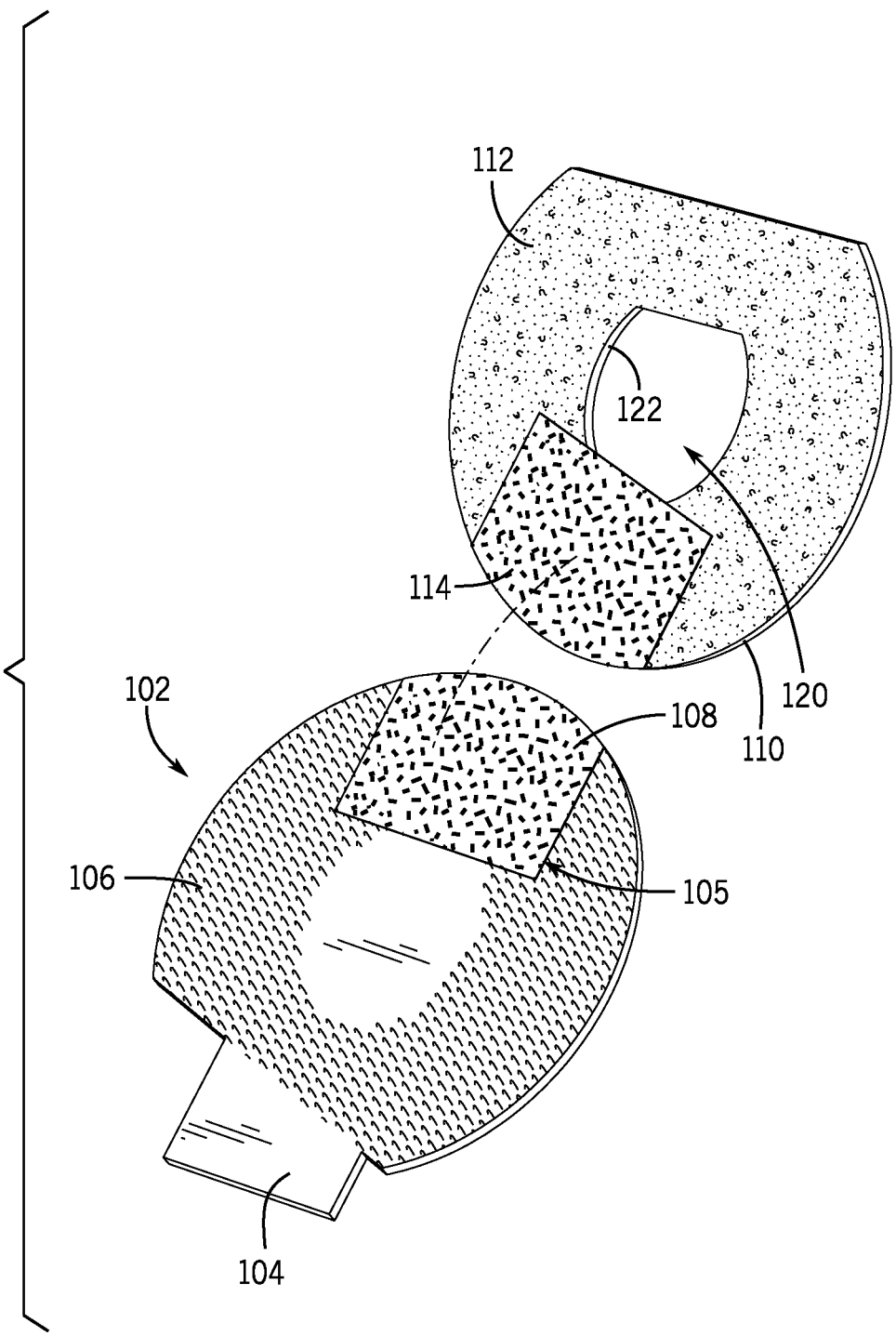
FIG. 3 is a perspective view of the bandaging system of FIG. 2 with its lid separated from its base to show special hinging areas.

FIG. 3 is a perspective view of the bandaging system of FIG. 2 with its lid 102 separated from its base 110 to show areas not visible in FIG. 2 which support the desired functioning of the hinge 105. The lid fastener 106 and the lid enhanced fastener 108 are designed to adhere to the base fastener 112 and the base enhanced fastener 114, respectively, in order to fasten the lid 102 to the base 110 when the bandaging system is closed. When the bandaging system is closed but needs to be opened to provide access to the wound region 120, moderate force sufficient to overcome the adhesive force between the unenhanced fasteners 106 and 112, but not the adhesive force between the enhanced fasteners 108 and 114, can be applied in order to obtain the configuration shown in FIG. 2. If stronger force sufficient to also overcome the adhesive force between the enhanced fasteners 108 and 114 is applied, one can obtain the configuration shown in this figure with the lid 102 entirely separated from the base 110. There are many art recognized ways to provide an enhanced fastener including using a different grade of hook and loop fastener.

Figure 4:
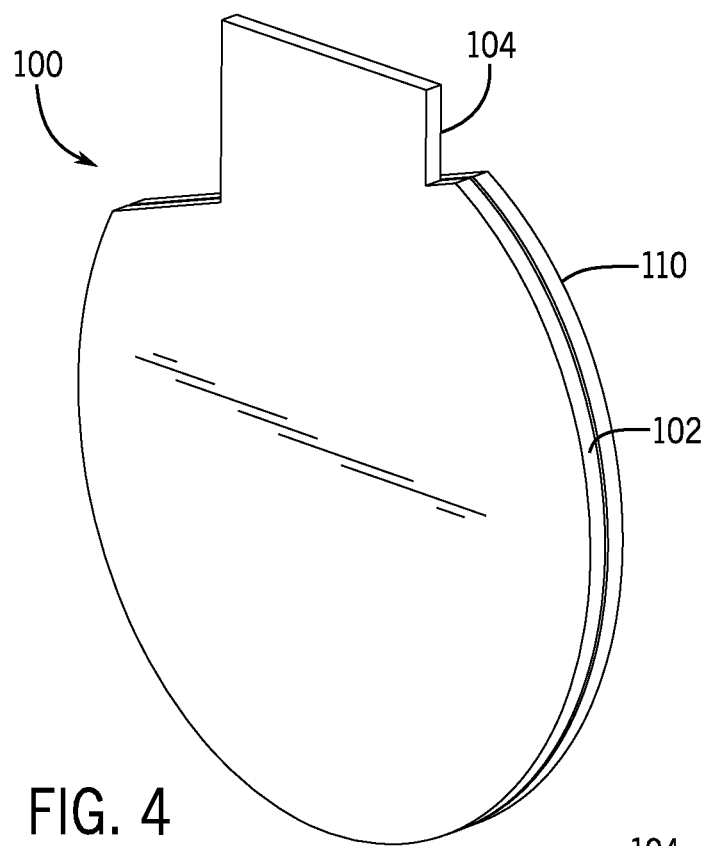
FIG. 4 is a perspective view of the assembled bandaging system of FIG. 2.

FIG. 4 provides a view of the upper side of the lid 102 of the bandaging system 100 in FIG. 2 after the bandaging system 100 has been closed, so that the lid 102 completely covers the base 110.

Figure 5:
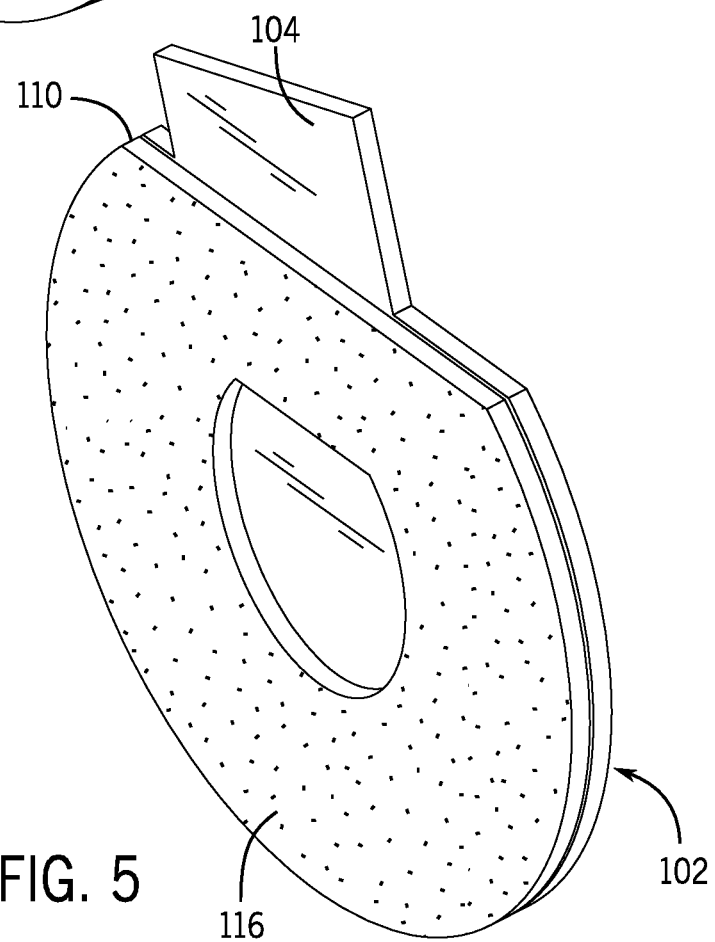
FIG. 5 is a perspective view of the other side of the assembled bandaging system of FIG. 4, showing the bottom surface of the base of the bandaging system that adheres to the skin of the patient.

FIG. 5 provides a view of the bandaging system 100 in FIG. 4 after it is turned around to display the bottom of the base 110, which is designed to be attached to the patient's skin. The base carries a typical bandaging adhesive 116 on its generally planar bottom side. The bandaging adhesive 116 may be any of those know to the art for securing bandaging materials to human skin without the need for additional securement material. The goal is that the base 110 will remain securely attached to the skin of the human patient 10 (shown in FIG. 1) while the lid 102 is repeatedly removed and resecured to the base 110, while still allowing the base 110 to be removed from the skin of the human patient 10 without undue pain or significant injury to the skin.

Adjusting the Size and Shape of a Banj Simple Bandaging System

Banj Simple bandaging system can be manufactured in a variety of sizes and shapes. To provide additional convenience and flexibility, the size and shape of a Banj Simple bandaging system made with velc or other suitable material can be adjusted to fit a particular wound by cutting it with scissors. Thus, one can easily be equipped to bandage a great variety of wounds without keeping a large inventory of bandages.

To facilitate such adjustments, packages of Banj Simple bandaging systems can contain pattern papers, which are pieces of paper with exactly the same shape as the bases of the Banj Simple bandaging systems in the package. Each of these will have a small central hole, which facilitates getting started on cutting out the shape of the wound region.

We now provide some directions for a caregiver who wishes to modify an available Banj Simple bandaging system to fit a particular wound. Use scissors, such as embroidery scissors, which are suitable for this task. Consider whether the skin around the wound which will be covered by the base should be cleaned or shaved. Start with a Banj Simple bandaging system which is sufficiently large and has a sufficiently small wound region. Note that the grip on the Banj bandaging system will be opposite the hinge. Decide where you would like these to be in relation to the wound. Use one of the supplied pattern papers to make a pattern for the base as directed below. Incrementally enlarge the center hole in the pattern paper until its edge provides a good boundary for the wound. Check that the pattern paper fits properly over the wound. On the pattern paper draw a line where you think the outer edge of the base should be. This can look like an enlarged version of the boundary, but you can make adjustments for relevant features of the patient's skin. When you are satisfied with this pattern for the base, cut the paper pattern along the line you have drawn for the outer edge of the base. Using the pattern as a guide, cut the base of the existing Banj Simple bandaging system to produce the base of the new Banj Simple bandaging system. Check that the base you have created will fit properly around the wound. Using the outer edge of the pattern as a guide, cut the outer part of the lid of the existing Banj Simple bandaging system to produce the lid of the new Banj Simple bandaging system. Do not cut away any material near the center of the lid. Also, depart from the guidance of the pattern to include in the new lid material for a grip. Remove the covering from the adhesive on the bottom of the base, and carefully affix the base to the patient's skin around the wound. After putting appropriate medication and dressing on the wound, place the lid on the base. When it is time to uncover the wound, pull up the grip.

Pressure on the Skin

Downward or upward pressure on a portion of the base may be produced when the lid is attached to the base, or released from it, while using a Banj Simple bandaging system. This does not happen with the other two models of the Banj bandaging system.

Banj Box Bandaging System

A Banj Box bandaging system features a low plastic ridge or wall called the base-wall which is on the boundary and surrounds the wound. This wall consists of three sections two of which are of the same height, which form concentric walls around the wound, and are adjacent to each other. The inner and outer sections, and the bottom portion of the middle section, are composed of base plastic and are attached to the rest of the base. These sections are called the inner base-wall, the middle base-wall, and the outer base-wall, respectively.

The main part of the lid is the lid-top, which covers the entire region bounded by the outer edge of the wall, and whose edges rest on the top of the wall. The edge of the lid-top is made of plastic, which we call lid plastic, and the central part of the lid may be plastic or anything else. Attached to the lid-top and extending downward is a wall of lid plastic (called the lid-wall) which is the upper portion of the middle section of the wall. The bottom edge of the lid-wall fits perfectly onto the top edge of the middle base-wall. We may refer to the base-wall or one of it sections as an upstanding wall, and refer to the lid-wall as the depending lid-wall. The lid consists of the lid-top and the lid-wall.

Base plastic and lid plastic may actually be the same kind of plastic, but they need not be. (Experiments may show that it is better to have certain parts of the middle section of the wall filled with base plastic all the way to the top, with corresponding adjustments in the lid.)

A package Banj bandaging system might resemble a carton and be mostly composed of cardboard, but it would have the plastic structure described above, about an inch high, attached to the top of the cardboard portion to provide an interface with the lid.

The Interface Between the Lid and the Base

To facilitate placing the lid on the base, the angles between the tops and sides of the inner base-wall and the outer base-wall which are adjacent to the middle section are not right angles but are cut at an angle so that at the very top of the wall, the space between the inner and outer sections of the wall is a little larger than it is farther down. Similarly, the bottom of the lid-wall will be narrower than it is higher up. (See FIG. 7) Of course, the lid still fits perfectly onto the base, as illustrated in FIG. 7.

Raising the Lid

At grips, the lid extends beyond the outer edge of the outer base-wall, so there is room for a finger, or the Key described later to catch the edge of the lid.

FIG. 6 is an illustration of a bandaging system 100 in which the lid 102 can be attached to and detached from the base 110 without exerting force on the skin of the human patient 10 (shown in FIG. 1) that surrounds the wound 20 (shown in FIG. 7). The base 110 has an upstanding base-wall 130 that interacts with and supports the lid 102. This upstanding base-wall 130 is provided with a rocker-lock assembly 140 that facilitates securing the lid 102 to the upstanding wall 130. The rocker-lock assembly 140 has a housing 141 which carries an unlocking aperture 142 and a locking aperture 143.

FIG. 7 is a cross section of FIG. 6 along line 7-7 which illustrates the mating of the depending lid-wall 103 of the lid 102 with the upstanding base-wall 130 of the base 110. The upstanding base-wall 130 consists of an inner base-wall 132, a middle base-wall 134, and an outer base-wall 136. The middle base-wall 134 has a lower height than the inner base-wall 132 and the outer base-wall 136, thus facilitating the aforementioned mating.

Figure 8:
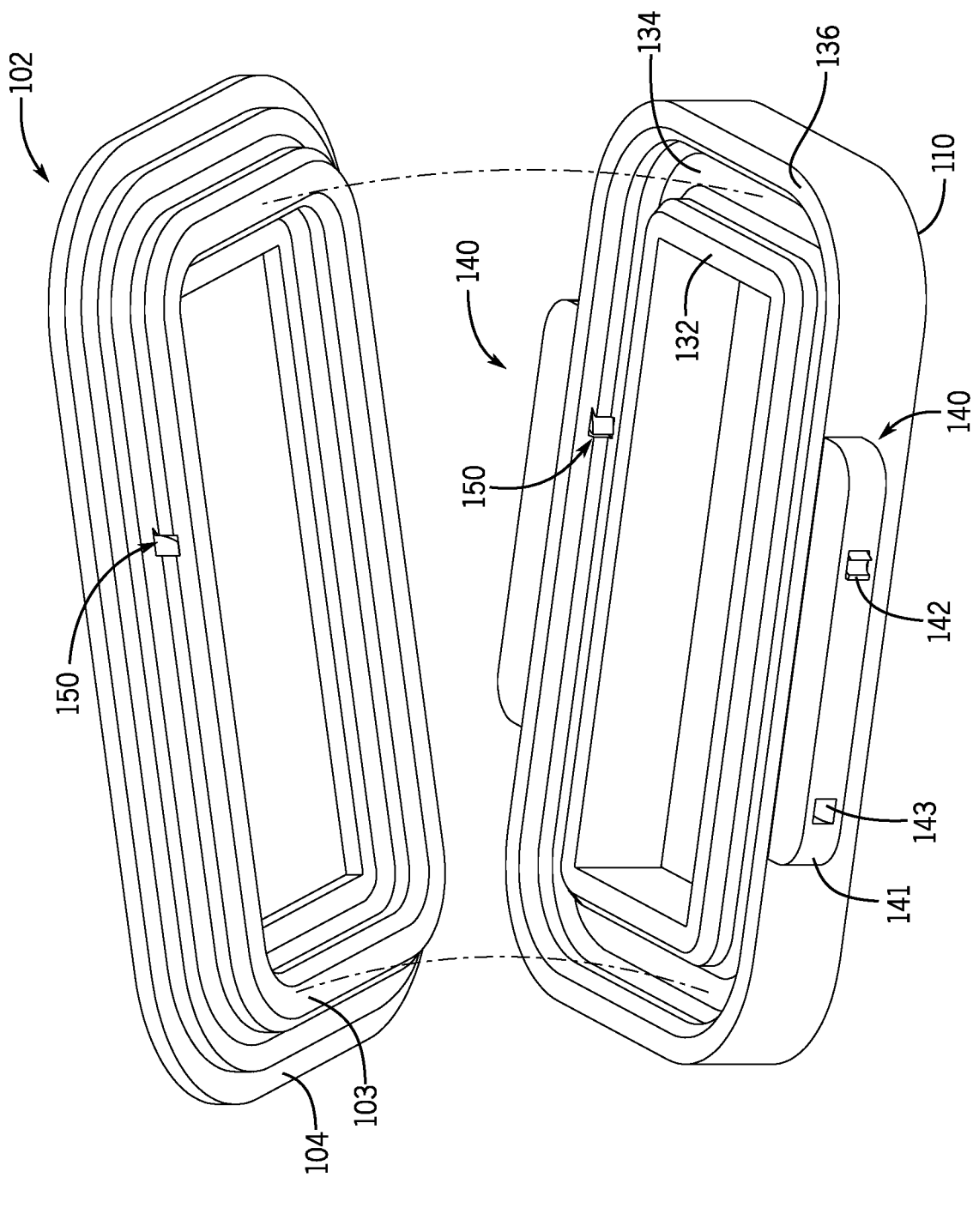
FIG. 8 is a perspective view of the embodiment of the bandaging system of FIG. 6 with the lid separated from the base.

FIG. 8 is a perspective view of the embodiment of the bandaging system of FIG. 6 with the lid 102 separated from the base 110. The depending lid-wall 103 mates with the inner base-wall 132 and the outer base-wall 136 of the upstanding base-wall 130 (shown in FIG. 6) and sits on top of the middle base-wall 134. The lid 102 also has a grip 104 by which it can be grasped when removing the lid 102 from engagement with the base 110. The base carries two rocker-lock assemblies 140. Each rocker-lock assembly has a housing 141, an unlocking aperture 142, and a locking aperture 143. Both the lid 102 and the base 110 have a locking pin engagement aperture 150, whose function will be more readily apparent from FIG. 9 and FIG. 9A.

Securing the Lid with Rocker-Locks

Once the lid is in place, it will be kept there by one or more rocker-locks. There is a locking pin which goes through the upstanding outer base-wall and the depending lid-wall when the lid is closed and locked in place. The locking pin can be moved in or out of locking position by simply pressing an appropriate button on a rocker-lock, which is a lever which is attached to one end of the locking pin and resides in a housing on the outside of the upstanding outer base-wall.

The Locking Mechanism

We start by describing the locking mechanism. When the lid is in place, a small peg (about as thick as a pin) which we shall call a locking pin goes horizontally through a hole in the outer and middle sections of the wall at a spot where the middle section is part of the lid. The lid cannot move while the locking pin is there. If the locking pin is withdrawn slightly, so that it does not extend as far as the middle section, the lock is off, and the lid can be moved. Very slight irregularities in the locking pin and the hole may prevent the locking pin from accidentally sliding in or out.

The Rocker

A rocker-lock is a three-dimensional object, but it can be cut out of a suitably thick flat sheet of plastic, so to describe a rocker-lock it suffices to describe its appearance as a figure drawn on a flat sheet. We first describe a rocker. Picture a plastic letter capital "V". We label the point at the upper end of the left line "L", the point at the upper end of the right line "R", and the point at the bottom where the lines meet "M". The plastic pieces from L to M and from R to M are rigid, but the junction at M is flexible. Keeping the position of M fixed, pull L and R down so that the angle at M becomes larger, but stop a little before LMR becomes a straight line. Now freeze the angle at M so that it can no longer change. We shall call the resulting piece of plastic a rocker. The portion of a rocker from M to R is called the locking arm of the rocker, and the portion from L to M is called the unlocking arm of the rocker.

Using the Rocker for a Locking Mechanism

Assume that the locking pin we described above is in place, protruding slightly from the outer edge of the wall. We turn the rocker on its side and attach point R of the rocker to the outside end of the locking pin. The rocker with the locking pin attached is called a rocker-lock. The rocker-lock should be placed so that the point M touches the wall, and L, M, and R and the entire locking pin are all at the same height above the base. (The provision that the rocker-lock is placed in a horizontal position, with L, M, and R all at the same height above the base, is generally the most appropriate arrangement, but it is not essential.) Note that pushing the point R in (toward the wound) pushes the locking pin in and locks the lid in place, while pushing the point L in pulls the locking pin out and unlocks the lid.

Curves Make the Lock Work Smoothly

Of course, a minor adjustment is necessary to make this work smoothly. The locking pin should be curved to the shape of an arc of a circle centered at M with radius the length of MR, and the hole for the locking pin should have the same shape.

The Rocker Housing

The rocker-lock is encased in a housing, which may be made of base plastic and attached to the outer side of the outer base-wall. The housing has holes to provide external access to the ends of the rocker. The housing is designed to permit the arms of the rocker to move within the plane which contains L, M, and R just enough to lock and unlock the lid, but not to move in any other way. Since each rocker-lock is hidden in its housing, all one will see of a rocker-lock is the outside of the housing.

Size Considerations

A major design objective affecting the sizes of various components is that the wall be as low as possible while conforming to the requirements that structures are strong enough, the lid slides easily into place if one places it almost correctly, and it is easy to remove the lid and to use rocker-locks.

A Key for the Lock

Description of a Rocker-Lock Key

To facilitate keeping certain components small, a small and simple plastic tool called a rocker-lock Key can be provided to help remove lids and press in the ends of rocker-locks. Appropriate Keys should be included in each package of Banj Box bandaging systems. At the center of a Key is a handle which is about the shape and size of a nickel coin. One end of the Key, which we call the engagement end, can be used to push in either end of the rocker arm. It is curved so that it slides easily into the tube through the housing at the end of the rocker arm.

The Lid Lifting End of a Rocker-Lock Key

The other end of the Key. which we call the lid lifting end, can be used to raise the lid. One will be able to slip the tip of the lid lifting end under the edge of the lid at a grip and pull up to raise the lid. If there is a small hole through each grip, the tip of the lid lifting end of the Key consists of a little hook which can catch the grip at the hole. The hook is thinner than the diameter of the hole. If there is no such hole, the tip of the lid lifting end resembles a miniature garden hoe.

If the Banj Box bandaging system has two grips which are opposite each other and not too far apart, the lid lifting end of the Key resembles a pair of tweezers. Using only one hand, a caregiver can grasp both grips and pull up on them simultaneously.

Figure 9:
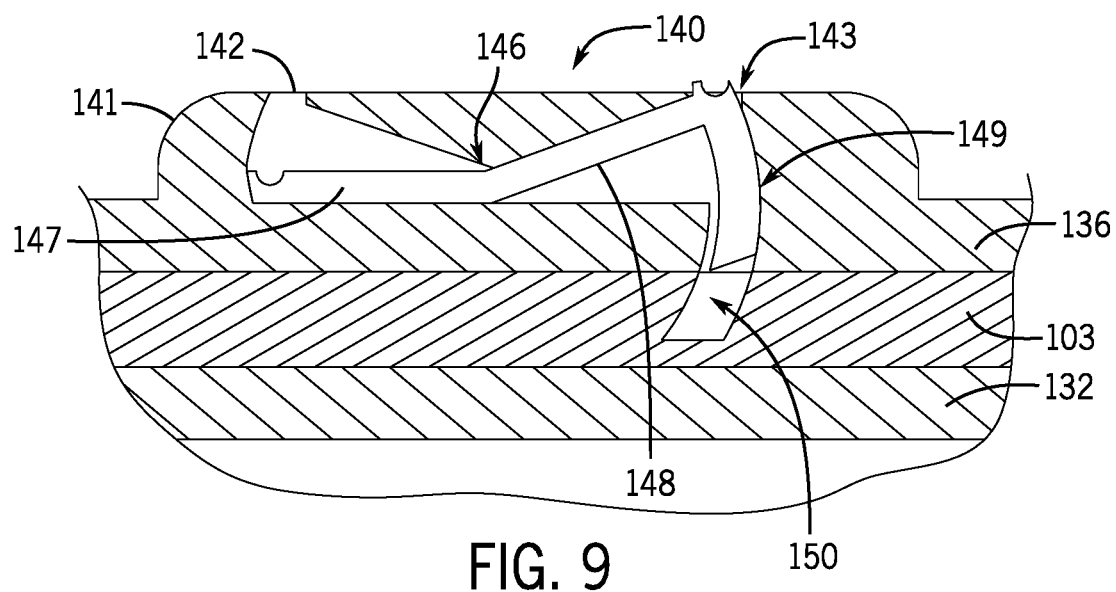
FIG. 9 is a cross section of the base carrying a rocker-lock assembly and being mated to a depending lid-wall.

FIG. 9 illustrates the interaction between the rocker-lock assembly 140 and the inner base-wall 132 and the outer base-wall 136 of the upstanding base-wall 130 and the depending lid-wall 103. The rocker-lock assembly 140 has a housing 141 which is attached to the outer base-wall 136. This housing has an unlocking aperture 142 and a locking aperture 143 and contains a rocker-lock 146. The rocker-lock 146 has an unlocking arm 147, a locking arm 148 and a locking pin 149. This locking pin 149 interacts with a locking pin engagement aperture 150 in the depending lid-wall 103. In this illustration the rocker-lock 146 is in an unlocked configuration where the locking pin 149 has not entered into the locking pin engagement aperture 150.

Figure 9A:
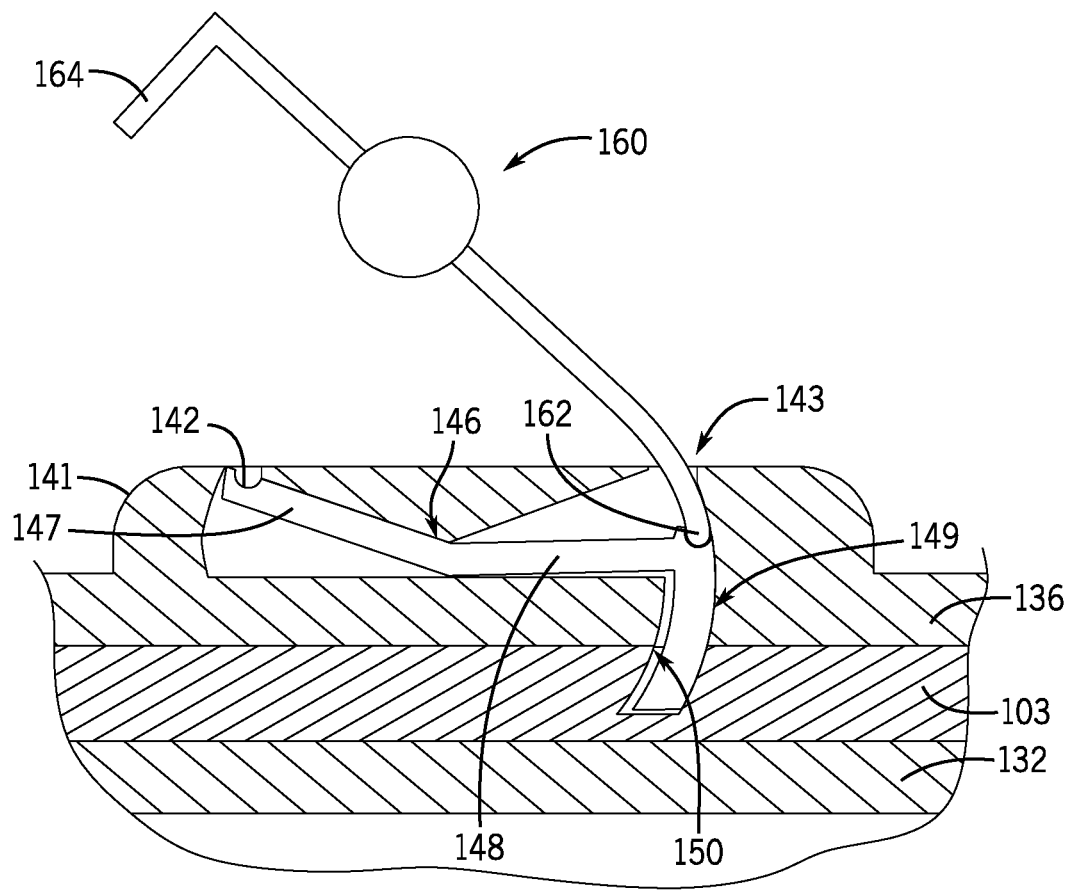
FIG. 9A is a cross section of the base carrying a rocker-lock assembly and being mated to a depending lid-wall that the rocker-lock has engaged by the use of a rocker-lock key.

FIG. 9A is an illustration of the rocker-lock 146 in a locked configuration in which the locking pin 149 has passed into the locking pin engagement aperture 150. The rocker-lock locking arm 148 has been moved into a locking position by the action of a rocker lock Key 160 via the rocker-lock Key engagement end 162. The rocker lock unlocking arm 147 is in position beneath the rocker-lock unlocking aperture 142 so that the rocker-lock 146 could be readily moved into an unlocked configuration through the action of the rocker-lock Key 160 via its engagement end 162. The Key 160 is also provided with a lid lifting end 164 that facilitates removing the lid 102 from the base 110 via the grip 104 (shown in FIGS. 7 and 8).

Dispensing with the Key

There may be situations in which a caregiver finds it inconvenient to keep a rocker-lock Key handy. To accommodate such situations, we now describe a variant of Banj Box bandaging system called Banj Box Keyfree bandaging system for which a Key is not needed. To avoid confusion, the version which we have previously described will be referred to as Banj Box Keylock bandaging system. The Keyfree version is obtained by adding buttons to the ends of each rocker-lock.

As we shall use the word in this document, a button has a top which is designed to be pressed by a finger, and a stem, which can be used to connect the top of the button to something else. The height of the button is the distance from the bottom of the stem to the top of the button. A button on a rocker-lock will be called the locking button or the unlocking button, depending on the arm of the rocker-lock to which it is attached.

When a button at an end of a rocker-lock is in position to be pushed in, that button protrudes from the housing just enough so that pushing the button in until it is flush with the housing will move the rocker-lock exactly the right amount to accomplish its purpose. Thus, when using Banj Box Keyfree bandaging system, one can push in either end of the rocker-lock by using one finger and no Key. When necessary, grips will be a bit larger, so that one will not need the lid lifting end of a Key to raise the lid.

Figure 10:
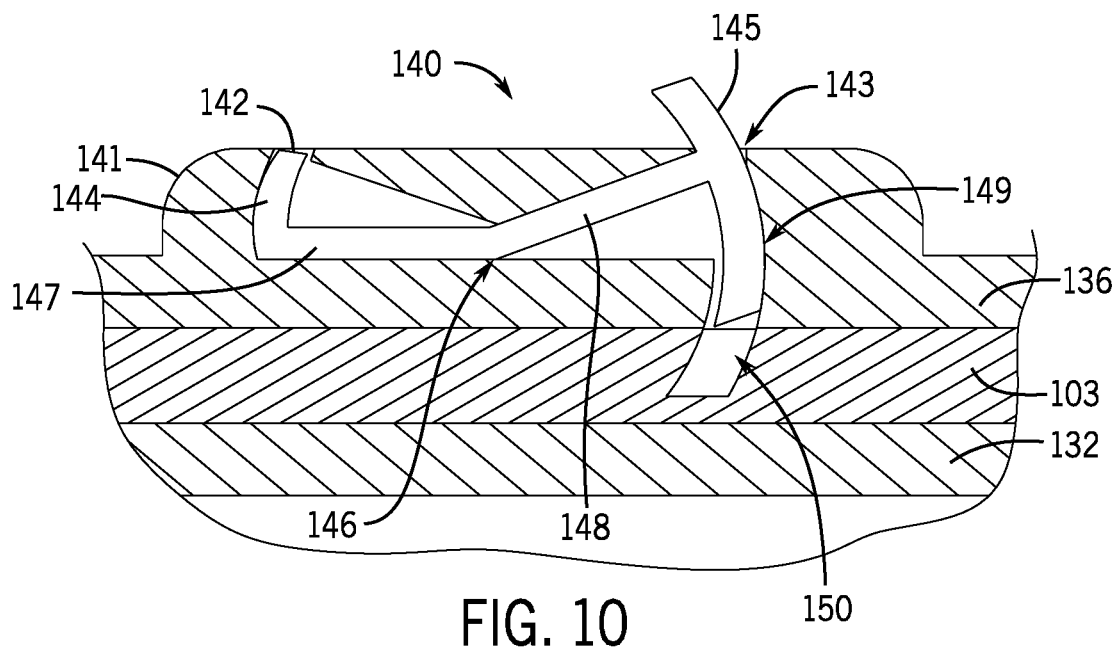
FIG. 10 is a cross section of the base carrying a rocker-lock assembly in which the rocker-lock has rocker-lock locking and unlocking arms of equal length and has locking and unlocking buttons and is mated to a depending lid-wall that the locking pin has not engaged.

FIG. 10 is an illustration of an alternative embodiment of a rocker-lock 146 which substitutes unlocking and locking buttons 144 and 145, respectively, for the use of Key 160. It is in its unlocked configuration in which the locking pin 149 has not protruded into the locking pin engagement aperture 150.

Figure 10A:
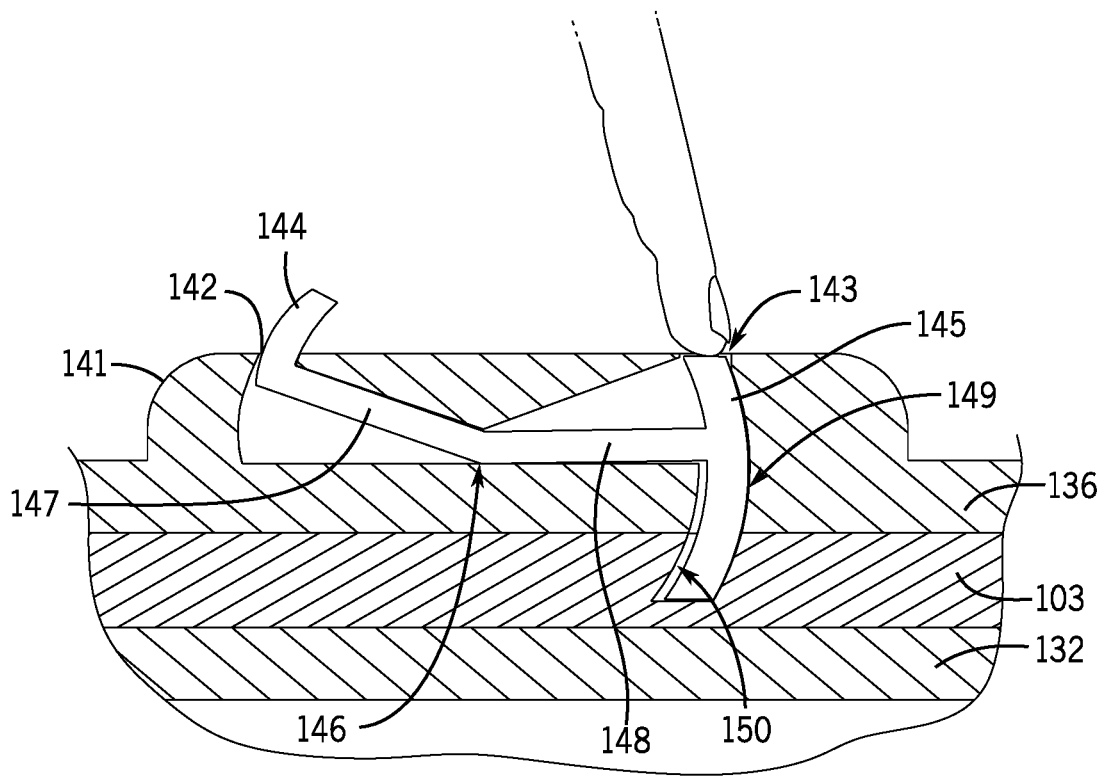
FIG. 10A is a cross section of the base carrying a rocker-lock assembly in which the rocker-lock has rocker-lock locking and unlocking arms of equal length and has locking and unlocking buttons and is mated to a depending lid-wall that the locking pin has engaged by the use of a finger

FIG. 10A is an illustration of the embodiment of the rocker-lock 146 of FIG. 10 in a locked configuration. A force has been applied to the rocker-lock locking button 145 by a human finger, causing the locking pin 149 to protrude into the locking pin engagement aperture 150.

Smoothing the Surface of a Banj Box Keyfree Bandaging System

The main challenge to the smoothness of the surface of a Banj Box Keyfree bandaging system is the fact that there is always a button which protrudes beyond the housing. The locking button, whose height is essentially the same as the width of the lid-wall, does not protrude from the housing when the lid is locked, so this button causes little concern, and we focus on minimizing the height of the unlocking button.

For the sake of simplicity and symmetry, in FIGS. 9, 9A. 10, and 10A the locking and unlocking arms of the rocker-lock are pictured as having the same length. However, they need not have the same length. We shall call a rocker-lock even if its arms have the same length, and odd in the contrary case.

Figure 11:
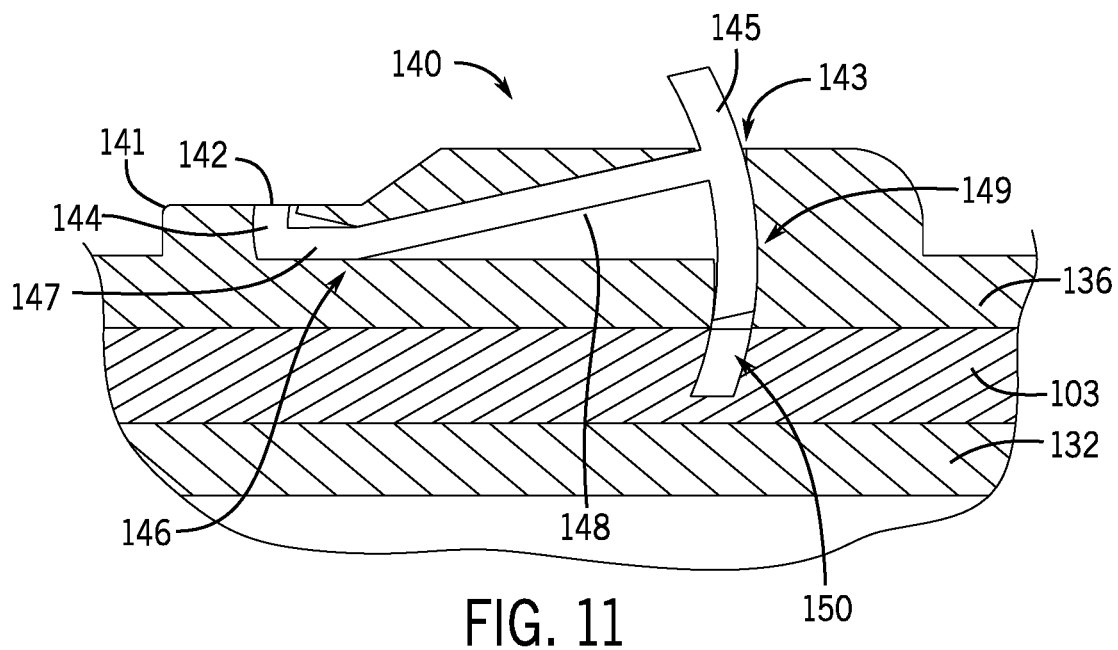
FIG. 11 is a cross section of the base carrying a rocker-lock assembly in which the rocker-lock has rocker-lock locking and unlocking arms of unequal length and has locking and unlocking buttons and is mated to a depending lid-wall that the locking pin has not engaged.
Figure 11A:
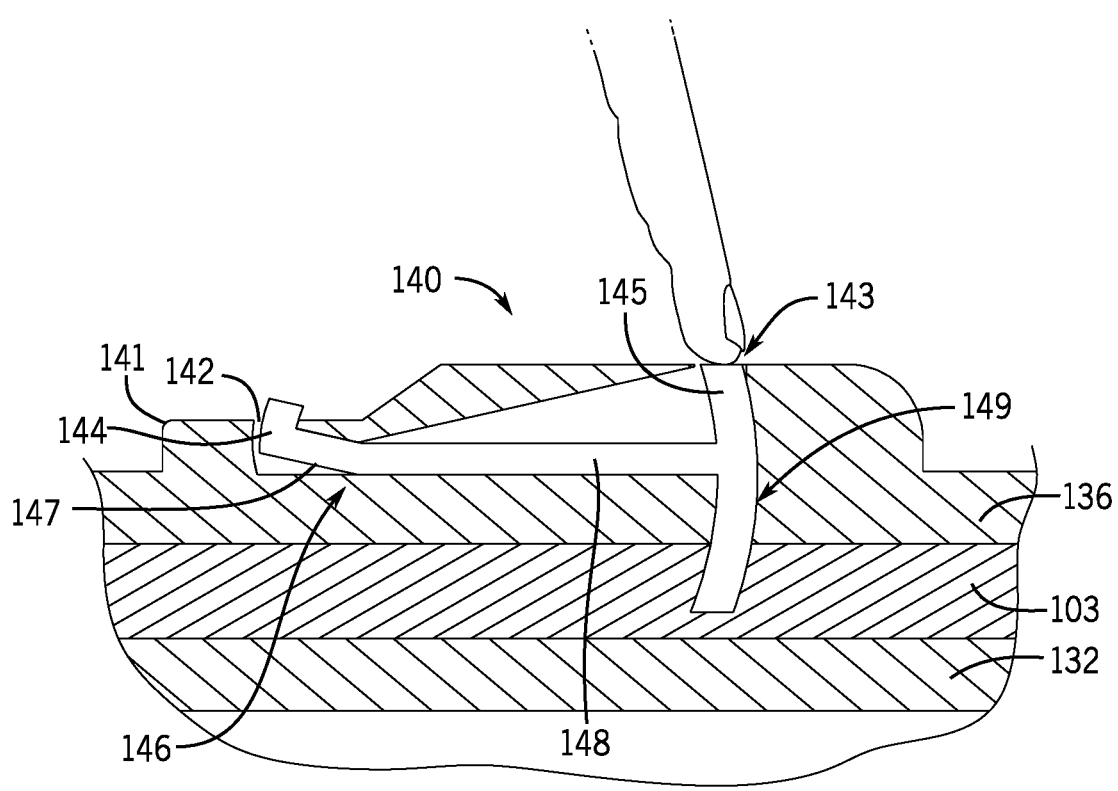
FIG. 11A is a cross section of the base carrying a rocker-lock assembly in which the rocker-lock has rocker-lock locking and unlocking arms of unequal length and has locking and unlocking buttons and is mated to a depending lid-wall that the locking pin has engaged by the use of a finger

FIGS. 11 and 11A display an odd rocker-lock for a Banj Box Keyfree bandaging system. Clearly, if the unlocking arm of the rocker-lock is much shorter than the locking arm, moving the unlocking end of the rocker-lock a small distance will cause the locking end to move much farther. In this situation, the unlocking button does not need to move very far in order to cause the locking end of the rocker-lock to move far enough to unlock the lid. Thus, the height of the unlocking button can be quite small if the unlocking arm of the rocker is much shorter than the locking arm. Compare the figures referenced above and note that the unlocking button protrudes much less from the Banj bandaging system with the odd rocker-lock.

These considerations are also relevant for Banj Box Keylock bandaging system. Making the unlocking arm of the rocker much shorter than the locking arm will reduce how far one must push the Key into the unlocking keyhole in order to unlock the lid.

FIG. 11 is an illustration of the embodiment of the rocker-lock assembly 140 in an unlocked configuration in which the rocker-lock unlocking arm 147 is shorter than the rocker-lock locking arm 148 and consequently the rocker-lock unlocking button 144 is shorter than the rocker-lock locking button 145.

FIG. 11A is an illustration of the embodiment of the rocker-lock assembly 140 of FIG. 11 in a locked configuration. Because of its shorter length the rocker-lock unlocking button 144, which should be compared with the unlocking button 144 in FIG. 10A, has a minimal protrusion from the rocker-lock housing 141. This minimizes the chance that it would scratch someone or be accidently activated to unlock the rocker-lock 146.

Choices

When considering the many forms a Banj bandaging system can have, no attention need be paid to the distinction between odd and even rocker-locks. The even-odd terminology was introduced only to facilitate explaining the benefit of making the unlocking arm shorter than the locking arm.

The Keyfree and the Keylock versions of Banj Box bandaging systems are closely related. If you start with a Keyfree version, cut off the buttons and use them for the engagement ends of rocker-lock Keys, you have a Banj Box Keylock bandaging system. Keyfree buttons protrude slightly, and Keylock necessitates keeping a Key (or some substitute) handy. Market experience will show the relative demand for each of these versions of Banj Box bandaging systems.

Designing the Rocker-Lock

A rocker-lock must be designed to work well on the particular Banj bandaging system where it will be used. Once the size and shape of the Banj bandaging system have been established, it should be easy to decide where the rocker locks should be and how long their arms should be. We describe how to design a rocker-lock for such a Banj Box Keyfree bandaging system. Similar methods will apply to a Banj Box Keylock bandaging system.

We shall use the name pivot point for the point M on the lower edge of the rocker-lock where the unlocking and locking arms meet. We shall use inner circle and outer circle as names for the circles centered at the pivot point with radii the lengths of the unlocking and locking rocker arms, respectively.

Since all parts of the rocker-lock maintain a fixed distance from the pivot point as the rocker-lock rotates around the pivot point, the locking pin and the locking button lie along the outer circle, and the unlocking button lies along the inner circle. When we say that an object such as a locking pin or button lies along a circle, we mean that the edge of that object which is closest to the pivot point is on that circle.

Step 1: Locking Pin and Locking Arm

Figure 12A:
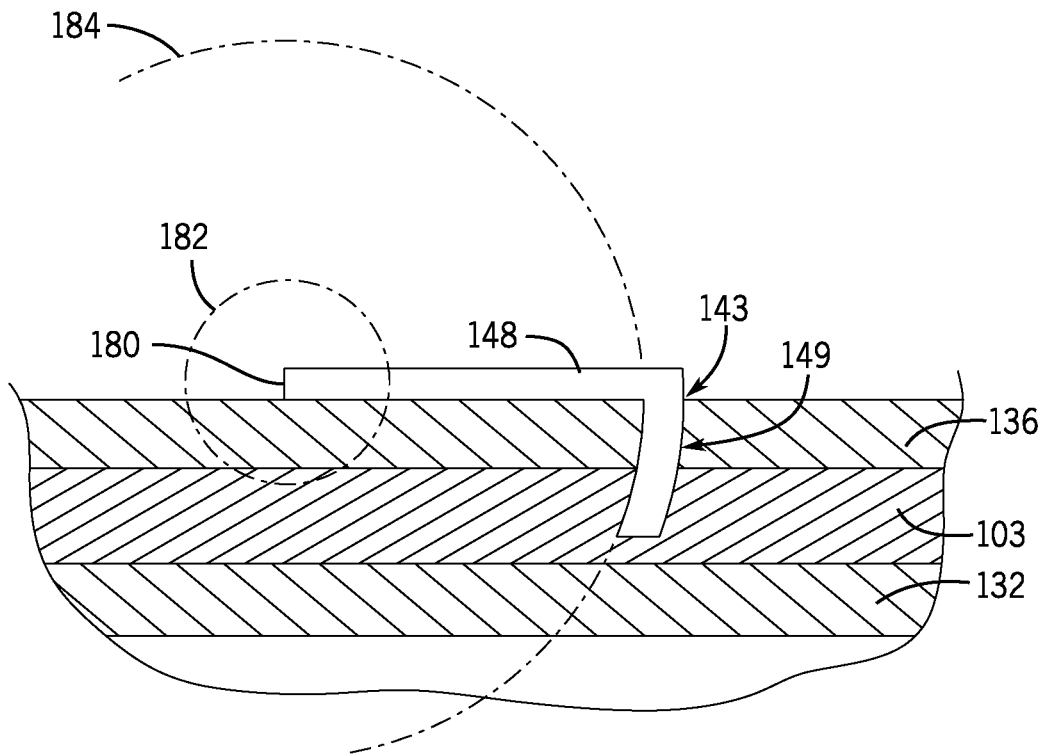
FIG. 12A illustrates Step 1 in the design of a rocker-lock with design circles and a cross section of the base mated to a depending lid-wall, showing the locking pin and locking arm of the developing rocker-lock.

Put the locking arm in place, lying adjacent to the outer wall, with one end at the pivot point and the other end on the outer circle. Put the locking pin in place along the outer circle, extending from the end of the locking arm to a point near the inner edge of the lid-wall. Attach these together rigidly where they intersect, so that the angle between the locking arm and the locking pin cannot change. We shall refer to this fragment of a rocker-lock as "the locking arm". We shall call the current position of the rocker-lock the locked position. FIG. 12A displays the current configuration. It remains to determine the angle between the unlocking and locking arms, and the lengths of the buttons.

Step 2: Unlocking Arm

Figure 12B:
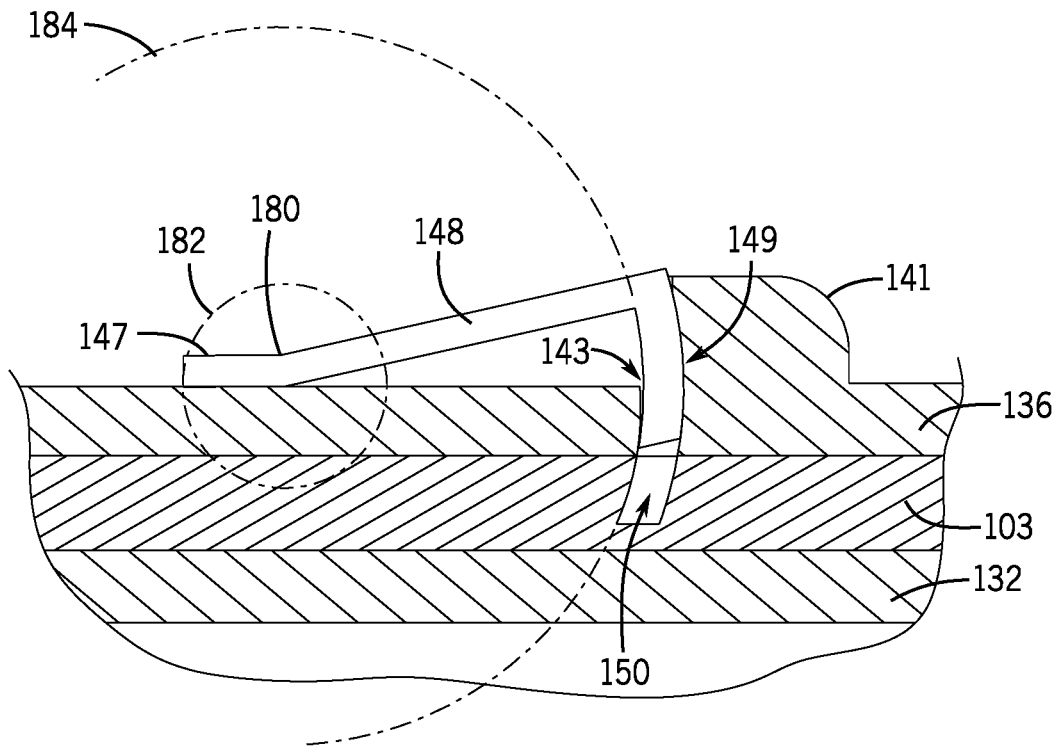
FIG. 12B illustrates Step 2 in the design of a rocker-lock with design circles and a cross section of the base mated to a depending lid-wall, showing the locking pin, locking arm, and unlocking arm of the developing rocker-lock.

Rotate the rocker-lock counter-clockwise until the end of the locking pin is just inside the outer wall. This puts the rocker-lock into what we shall call the unlocked position, since the lid is now unlocked. Create a fragment of the housing next to the locking pin, on the side of the locking pin farthest from the pivot point, extending from the outer wall to the level of the point where the locking pin meets the locking arm. Put the unlocking arm adjacent to the outer wall, with one end at the pivot point and the other end on the inner circle. Attach the unlocking and locking arms to each other rigidly where they meet at the pivot point, so that the angle between them cannot change. FIG. 12B displays the current configuration.

Step 3: Locking Button

Figure 12C:
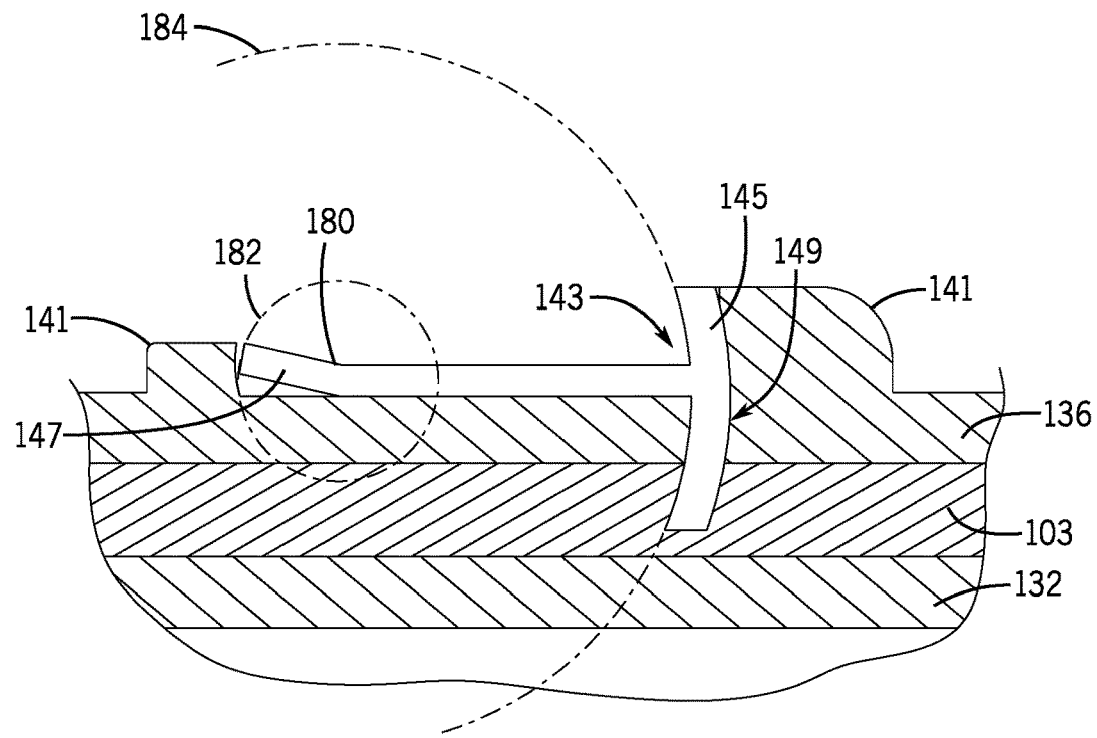
FIG. 12C illustrates Step 3 in the design of a rocker-lock with design circles and a cross section of the base mated to a depending lid-wall, showing the locking pin, locking arm, unlocking arm, and locking button of the developing rocker-lock.

Rotate the rocker-lock clockwise into the locked position. Create the locking button so that it lies along the outer circle and extends from the point where the locking pin meets the locking arm to the level of the housing fragment created in Step 2. Create a fragment of the housing next to the portion of the inner circle which meets the unlocking arm, on the side of the inner circle farthest from the pivot point, extending from the outer wall to the level of the point where the inner circle meets the unlocking arm. FIG. 12C displays the current configuration.

Step 4: Unlocking Button

Rotate the rocker-lock counter-clockwise into the unlocked position. Create the unlocking button so that it lies along the inner circle and extends from the point where the inner circle meets the unlocking arm to the level of the housing fragment created in Step 3. Adjust the edges of the housing fragments so that they do not overlap any parts of the rocker-lock.

Figure 12D:
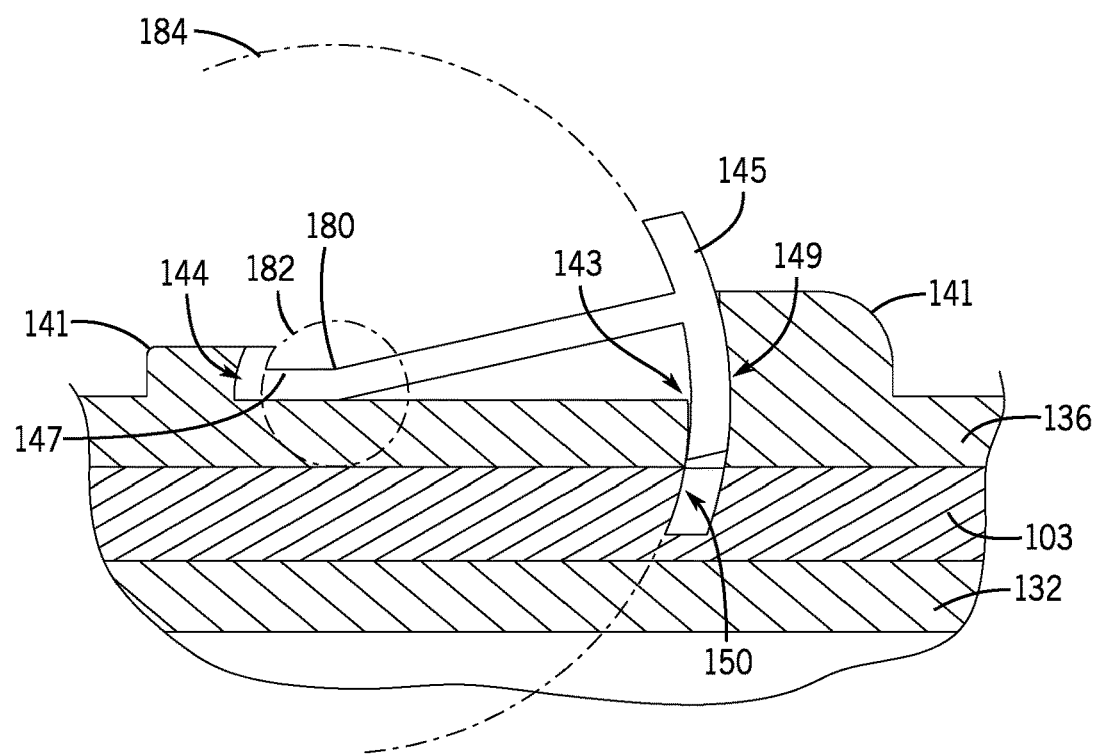
FIG. 12D illustrates Step 4 in the design of a rocker-lock with design circles and a cross section of the base mated to a depending lid-wall, showing the locking pin, locking arm, unlocking arm, locking button, and unlocking button of the completed rocker-lock.

FIGS. 12A-D illustrate steps in designing the embodiment of the rocker-lock assembly 140 illustrated in FIGS. 11 and 11A. In FIG. 12A the rocker-lock locking arm 148 is in the locked position with the locking pin 149 engaged with the depending lid-wall 103. The locking pin 149 has been rigidly attached to the rocker-lock locking arm 148. In FIG. 12B a portion of the rocker-lock housing 141 has been added with an inner edge that matches the curved outer edge of the locking pin 149. In addition the rocker-lock unlocking arm 147 has been added extending to the circumference of the circle 182. In FIG. 12C the rocker-lock locking button 145 has been added with its inner edge lying along the circumference of design circle 184 and a portion of the rocker-lock housing 141 has been added with an inner edge that also lies along the circumference of design circle 184. In FIG. 12D the unlocking arm 147 has been rigidly attached to the unlocking button 144 with inner edge of this button lying along the circumference of design circle 182.

This completes the construction of the rocker-lock. Of course, additional material must be added to the housing so that the rocker-lock can rotate freely between the locked and unlocked positions, but not move in any other way.

Banj Box Bandaging System Makes Things Comfortable and Simple

In summary, a Banj Box bandaging system lid is designed to slide on and off very smoothly, so there is no downward pressure or upward tugging on the base. The rocker-locks enable the lid to be locked into place or released quickly and easily. Thus uncovering and covering the wound is very comfortable for the patient and simple for the caregiver when a Banj Box bandaging system is used.

Banj Kwik Bandaging System

The Basic Design of Banj Kwik Bandaging System

Banj Kwik bandaging system is very similar to Banj Box bandaging system, but the boundary of a Banj Kwik bandaging system is always a rectangle, and there are hinges on two parallel edges of the rectangular lid-top. Normally the shorter edges have the hinges, but this is not essential. Since there are hinges at both ends of the Banj Kwik bandaging system, rather than at just one end, the caregiver does not have to initially decide which end should have the hinge, and on different occasions 'e can use whichever hinge is most convenient.

To describe a Banj Kwik bandaging system, we shall explain how one can be obtained by modifying a rectangular Banj Box bandaging system.

Install Hinges

The lid-wall of the Banj Box bandaging system has four straight sections, one for each side of the rectangle. Two sections on opposite sides of the rectangle will have hinges installed at their top edges. These will be called hinge-walls, and the other two sections will be called non-hinge-walls. Little strips of rigid plastic in the lid-top near the tops of the hinge-walls may be replaced by flexible plastic to form the hinges. The dimensions of the Banj bandaging system will not be changed.

Modify the Lid-Walls

Additional modifications of the lid for Banj Kwik bandaging system are motivated by the fact that when a hinge is used, each moving part of the Banj Kwik bandaging system lid moves in a circular arc, maintaining a constant distance from the hinge. Let r be the distance between the two hinge-walls (measured along a line perpendicular to them).

Each non-hinge-wall is modified as follows: all lid plastic in that wall whose distance from either upper corner of that wall is greater than r is replaced by base plastic. In other words, these parts of the lid are turned into parts of the base. Note that the indicated adjustment cuts apart the four straight sections of the lid-wall, so that these sections are not directly connected to each other, although they are all connected to the lid-top. The reason this is necessary is the same as the reason that if a square box Q is inside a fixed rectangular box R whose width is only slightly greater than the width of Q, then Q cannot be rotated 90 degrees.

Each hinge-wall is modified so that it lies along the outer edge of an imaginary cylinder of radius r whose axis is the hinge on the opposite wall. The base-walls adjacent to this lid-wall are modified with it, so that base-plastic surrounds the lid-wall in its new position and shapes the Banj Kwik bandaging system appropriately. See FIG. 13A. It is enlightening to compare FIG. 13A with FIG. 7. In a Banj Box bandaging system the lid-walls are straight, and in a Banj Kwik bandaging system they are shaped like arcs of a circle.

The Banj Kwik bandaging system produced by these operations has a different boundary than the Banj Box bandaging system we started with, but our objective was simply to describe a Banj Kwik bandaging system.

Raising the Lid

There are rocker-locks under each hinge. Before using a hinge to raise the lid-top, lock all rocker-locks under that hinge, and unlock all other rocker-locks. Then use a grip under the opposing hinge to raise the lid-top and the three lid-wall sections which are not under the hinge being used, using a motion which will permit each moving part of the lid to maintain its distance from the hinge. See FIGS. 13B-G. One can think of this process as rotating an imaginary cylinder which is centered at the hinge.

Figure 13A:
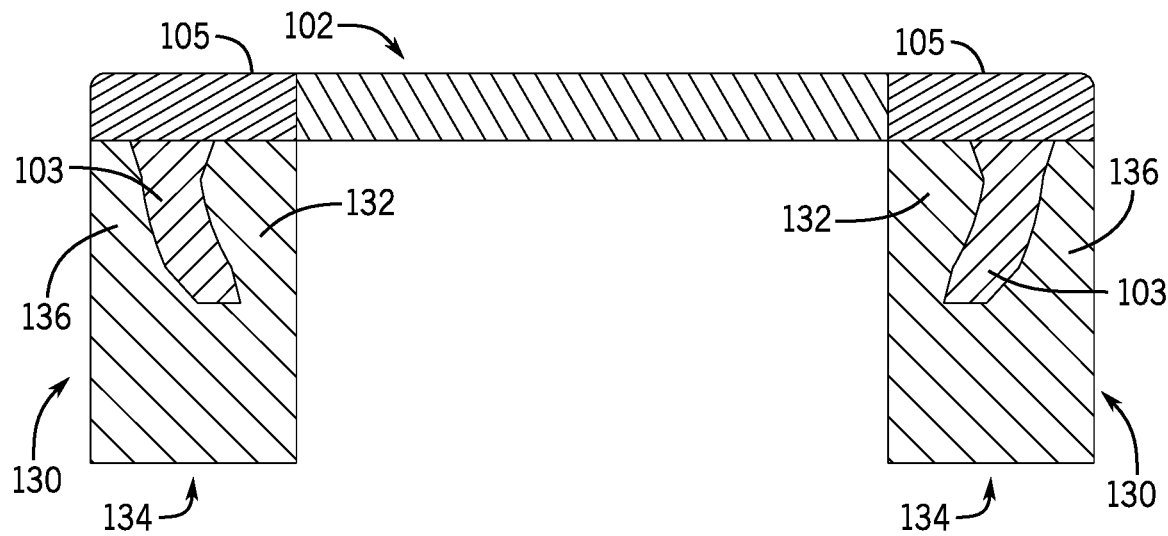
FIG. 13A is a cross section of a bandaging system with hinges in the lid and non-planar walls, with the lid closed.
Figure 13B:
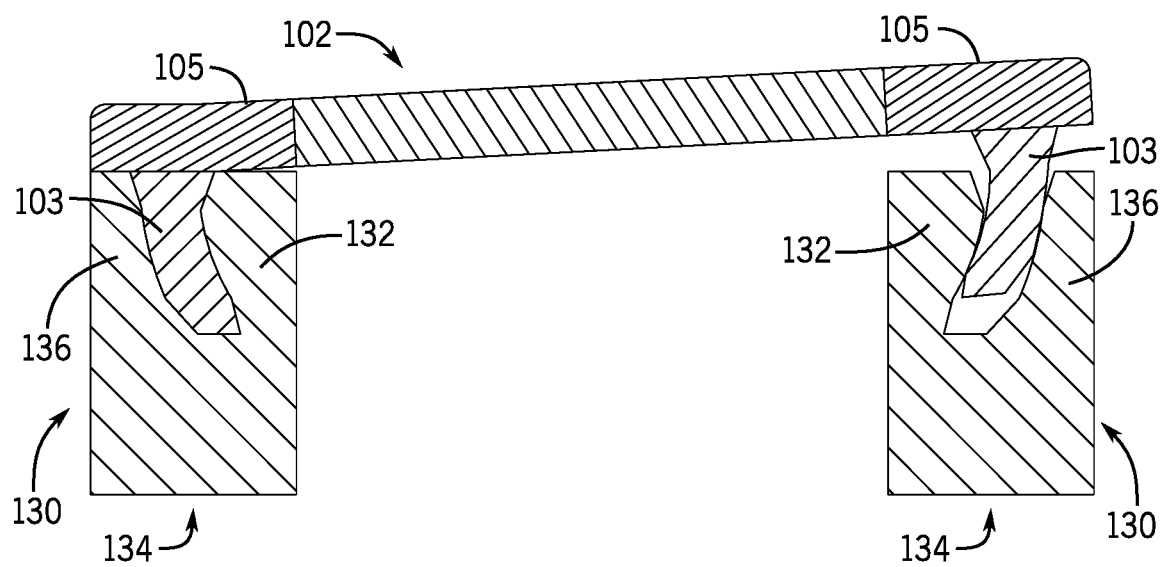
FIG. 13B is a cross section of a bandaging system with non-planar walls, showing one side of the lid starting to tilt up, as is enabled by a hinge in the opposite side of the lid.
Figure 13C:
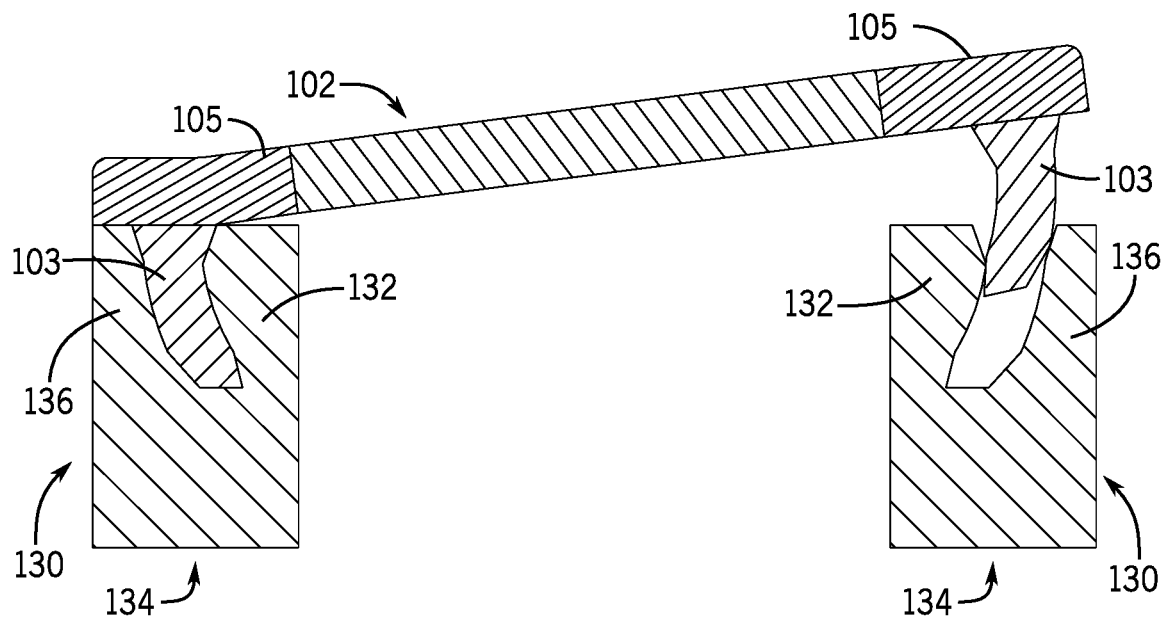
FIG. 13C is a cross section of a bandaging system with hinges in the lid and non-planar walls, showing how the curvatures of the walls enable the lid-wall to slide smoothly when the lid tilts up.
Figure 13D:
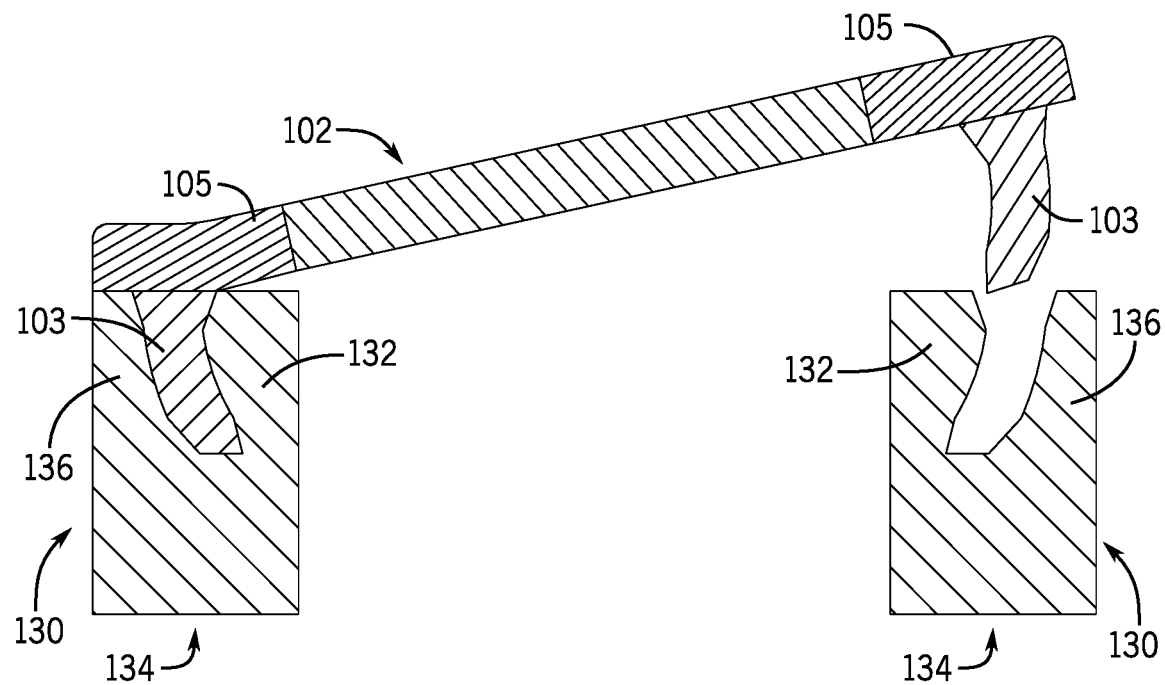
FIG. 13D is a cross section of a bandaging system with hinges in the lid and non-planar walls, with the right edge of the lid almost clear of the upstanding wall.
Figure 13E:
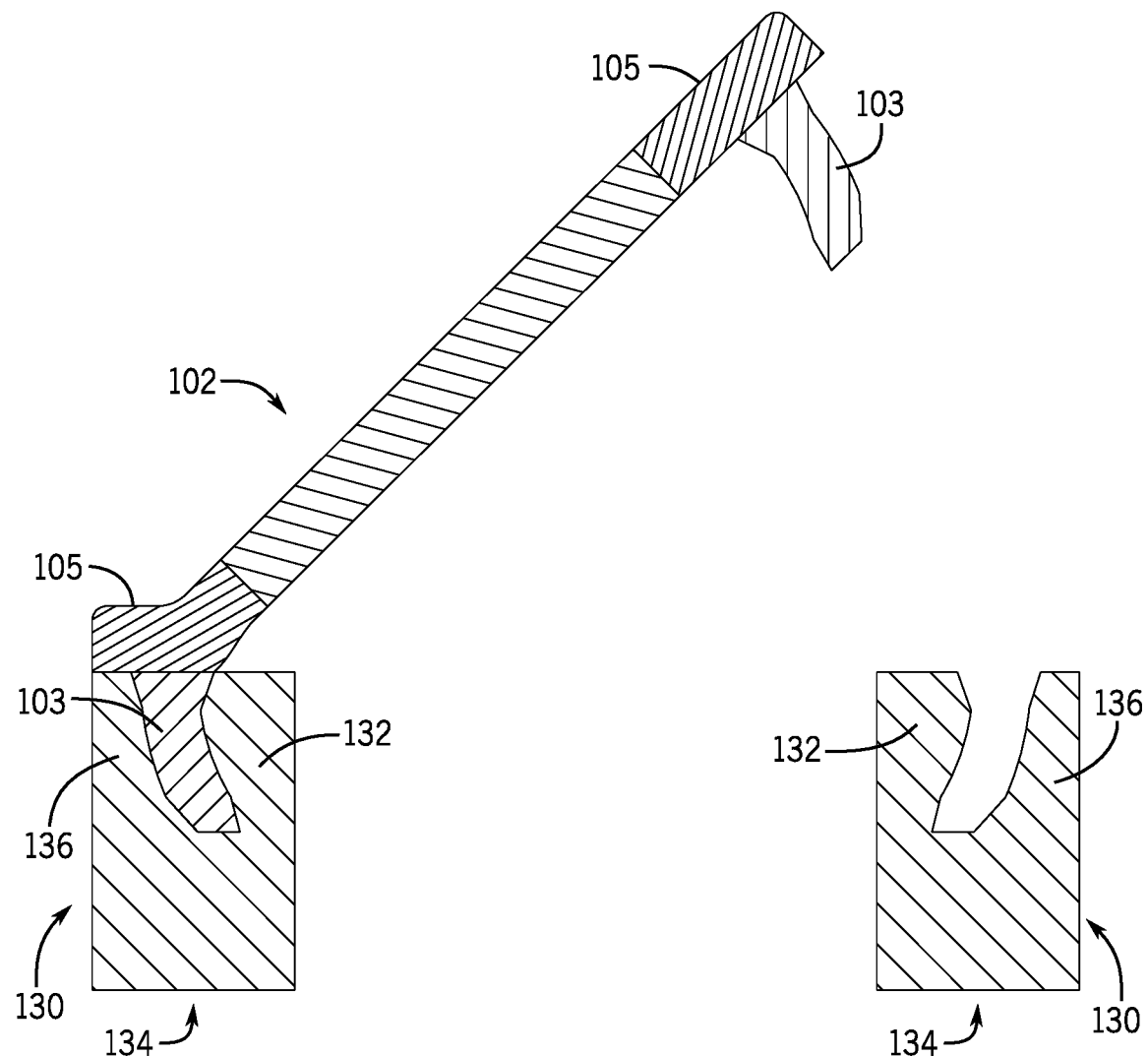
FIG. 13E is a cross section of a bandaging system with hinges in the lid and non-planar walls, with one side of the lid in a position substantially away from the upstanding wall on that side.
Figure 13F:
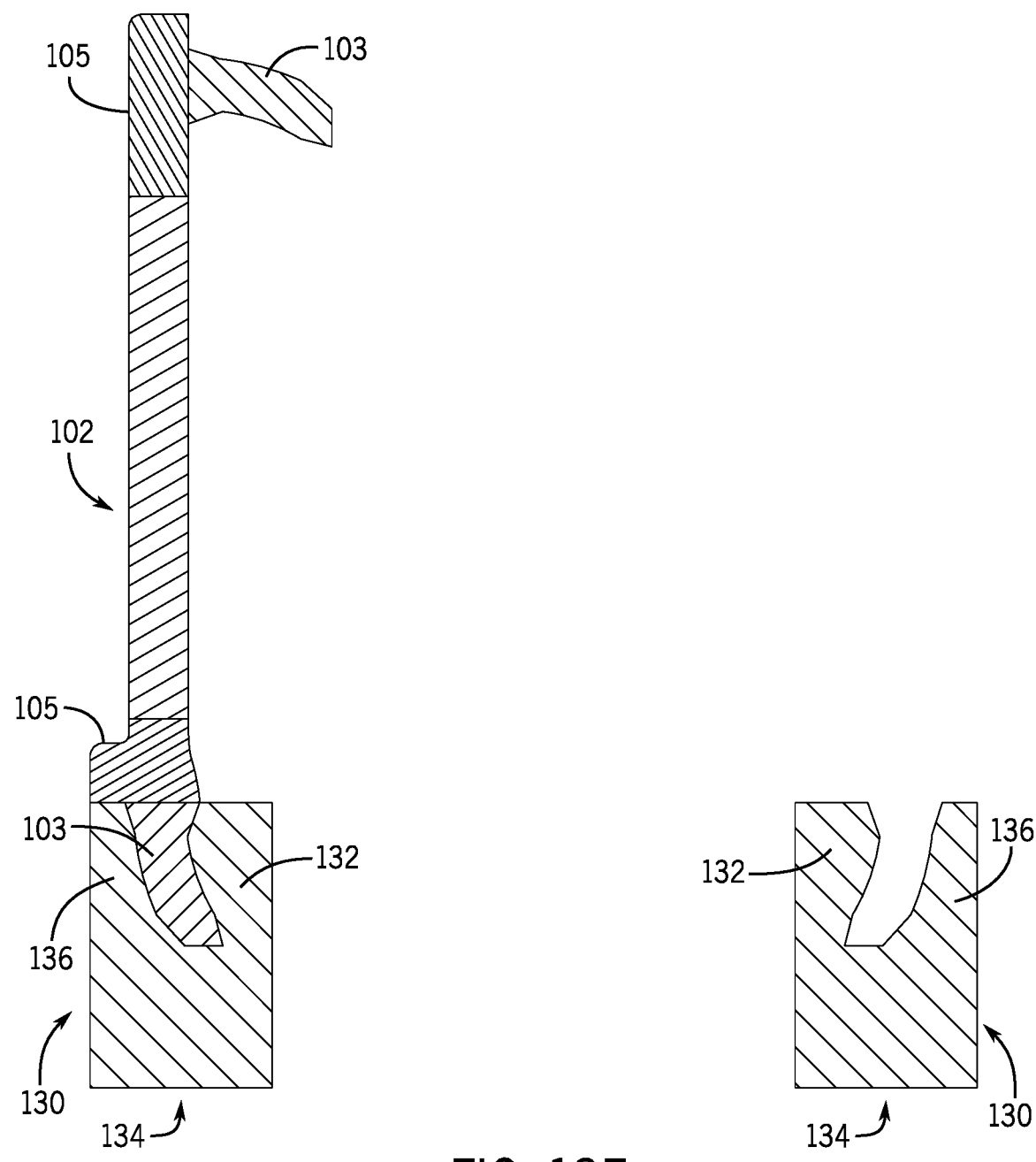
FIG. 13F is a cross section of a bandaging system with hinges in the lid and non-planar walls, with the lid in position to be removed entirely from the base.

If the lid is to be removed entirely, after executing the procedure just described to reach the vertical configuration shown in FIG. 13F, unlock all remaining rocker-locks, and pull out the hinge and the lid-wall section beneath it, using a motion which will permit each part of this lid-wall section to retain its distance r from the top of the opposing wall.

To install a lid, reverse this procedure.

Figure 13G:
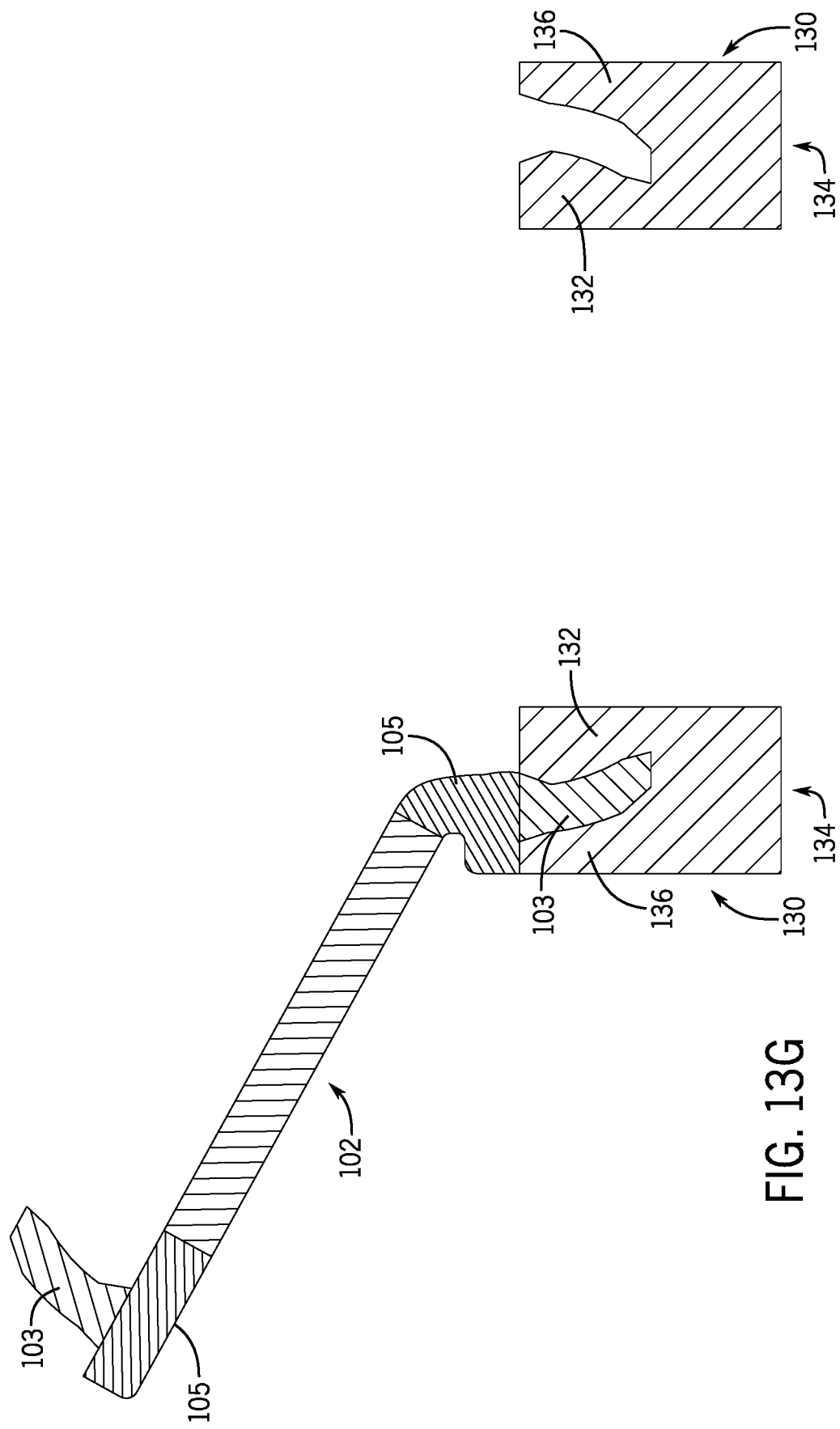
FIG. 13G is a cross section of a bandaging system with hinges in the lid and non-planar walls, with the lid folded back to provide good access to the wound.

FIGS. 13A-G illustrate an embodiment in which the lid 102 is opened to expose the wound region 120 (illustrated in FIGS. 1, 2, and 3) by a hinging action. In FIG. 13A the lid 102 is in closed position, having fully engaged the inside and outside portions 132 and 136, respectively, of the upstanding base-wall 130 via its depending lid-wall 103. In FIG. 13B the depending wall 103 has started to disengage from the upstanding base-wall 130 by using the flexibility of the material in the hinge 105 region of the lid 102. This region is constructed of a flexible material such as many of the common plastics. FIGS. 13C-G show the lid 102 continuing to open more, disengaging smoothly because of the curvatures of the walls. In FIG. 13G the lid 102 has bent far enough to provide ready access to the wound 20 (shown in FIG. 1).

Banj Kwik bandaging system makes things comfortable, simple, and quick.

Just as with Banj Box, uncovering and covering the wound is very comfortable for the patient and simple for the caregiver when Banj Kwik is used. These things can also be done even more quickly when Banj Kwik is used, since the hinges are so convenient. When a hinge is used, the lid is not detached, so it does not need to be re-attached.

Summary of Models

We have described various Banj bandaging systems and the rationales for their designs. Now we summarize what seem likely to be the best choices of Banj bandaging systems for various situations.

If a simple Banj bandaging system with a low profile suffices, and some upward and downward pressure on the skin near the wound is acceptable, use Banj Simple bandaging system. Otherwise, if the boundary is rectangular, use Banj Kwik bandaging system. Otherwise, use Banj Box bandaging system.

If Banj Kwik bandaging system or Banj Box bandaging system is used, a choice must be made between Keylock and Keyfree versions. A caregiver using Keylock needs to have a Key handy. When Keyfree is used, a button protrudes from the housing of each rocker-lock. This protrusion can be minimized by making the ratio between the lengths of the unlocking and locking arms of the rocker-locks as small as possible.

Summary of Features

Lids of Banj bandaging systems can be removed and then re-attached or replaced without detaching the base from the skin of the patient.

Banj bandaging systems are designed to be free of hidden hazards, comfortable for the patient, and quick and convenient for the caregiver to use.

All parts of a Banj Simple bandaging system are planar, so it has a very low profile.

A Band Simple bandaging system can be cut to exactly the desired shape.

Hinges in Banj Simple and Banj Kwik bandaging systems make it possible to examine and treat the wound without detaching the lid, but the lid can also be detached and then re-attached or changed.

Enhanced fasteners in a Banj Simple bandaging system make it easy when using the hinge to pull up one side of the lid just the right amount so that one does not accidentally detach the lid from the base.

When a Banj Box or Banj Kwik bandaging system is being used, no downward or upward pressure on skin near the wound is produced by attaching or releasing the lid.

The exposed tops and bottoms of the walls in Banj Box and Banj Kwik bandaging systems are shaped in a way that makes it very easy to place the lid on the base. If one puts the lid in approximately the correct place, it slides easily into exactly the desired position.

Banj Box bandaging systems are suitable for being produced by a system in which custom designed Banj Box bandaging systems are ordered by submitting a pattern for the base using a suitable technology, and the bandaging systems are delivered very promptly, or produced by a local 3-D printer.

The lid of a Banj Box or Banj Kwik bandaging system is secured to the base by one or more rocker-locks.

The locking pin and buttons of a rocker-lock are curved so that a gentle touch suffices to lock or unlock the rocker-lock.

The ratio between the lengths of the locking and unlocking arms of a rocker-lock in a Banj Box or Banj Kwik bandaging system is chosen to minimize the amount by which the unlocking button protrudes when the lid is locked to the base.

There are two hinges on the lid of a Banj Kwik bandaging system, so the caregiver can raise whichever end of the lid is most convenient on a particular occasion.

The smooth functioning of each of the two hinges on a Banj Kwik bandaging system is facilitated by the fact that all four sections of the lid-wall are shaped so that they lie along or inside an imaginary cylinder centered at the hinge with radius the distance between the hinges.

Alternative Designs

Persistent bandages can be designed in many ways, and it is natural to consider which designs are best. We may also ask what are the criteria for being best. Important criteria are provided by the interests of the patients and caregivers who will directly benefit or suffer from the way these bandages work, and whose reactions will determine how they fare in the market. If the patient's skin near the wound is sensitive, uncovering and covering the wound should involve no stressful actions such as pressing, pushing, pulling, or twisting. The caregiver will appreciate systems that are very easy and quick to use.

If a Banj bandaging system with a hinge is being used, the wound can be examined and treated without detaching the lid. A rocker-lock is controlled by a simple touch.

To facilitate comparisons while leaving detailed analyses to the reader, we now discuss some alternative ideas and technologies which are not used in the Banj bandaging systems described above, but which might be used to design persistent bandages. We shall not describe these ideas in detail, or discuss their merits, drawbacks, or exactly how they might be used. We shall simply present descriptions of them which may stimulate further thoughts about alternative designs of persistent bandages.

If a persistent bandage has a base and a lid as components, a major design issue is how the lid is to be latched to the base. In Banj bandaging systems, rocker-locks serve as latches. The ideas discussed below involve alternative latching mechanisms. When we refer to Banj bandaging systems below, we assume that all rocker-locks and housings have been eliminated from them.

Boxes

We consider designs in which the bandage has the basic form of a box (such as a shoe box) with no bottom. We can think of this structure, which we shall call a box, as the result of deleting the outer wall, and the lower part of the middle wall, from a Banj Box bandaging system or a Banj Kwik bandaging system. The lid-top of the Banj bandaging system is the horizontal part of the box cover, and the sections of the lid-wall of the Banj bandaging system are the vertical sides of the box cover. Latches can be designed using the ideas and devices listed below:

a miniature zipper;

clamps (like clothes pins or binder clips) mounted on the box wall which can grasp the edge of the cover;

a plastic bolt which can be screwed down to clamp a fixture on the edge of the lid to a fixture on the box wall beneath it;

a plastic hook attached to the edge of the lid which can swivel to catch a button on the box wall beneath it;

an elastic band attached to the edge of the lid which can be stretched to catch a button on the box wall beneath it; or if the box is round (and resembles a jar), the lid can simply be screwed on or off Banj Bandaging System Alternatives We describe persistent bandages which can be obtained from Banj Box bandaging systems and Banj Kwik bandaging systems by proceeding as follows. Remove most of the outer wall but leave vertical strips of the outer wall wherever there was a rocker-lock. Make the inner wall and the middle wall (which includes the lid-wall) quite rigid but let the strips of the outer wall be quite flexible. The lid will be locked by attaching the upper portion of each outer wall strip to the lid-wall adjacent to it. This may involve pressing and pulling, but this will all be horizontal pressure, not vertical pressure.

The attachment of the outer wall strips to the lid-wall will be accomplished by using simple technologies such as:

Velc or Setex® fasteners.

The groove and bead technology such as is used to seal sandwich bags.

Snaps such as are found on some garments such as jackets.

Horizontal ridges in the strips of the outer wall which fit into grooves in the lid-wall, and an elastic band which goes around the entire bandage near the top, holding the strips of the outer wall snuggly close to the lid-wall, so that the lid-wall cannot slide up while the elastic band is in place.

Example: Some Details Using Velc

As an example, we provide additional details for the alternative design involving flexible strips of the outer wall when the fastener is velc. The lid of the Banj bandaging system can be locked simply by pressing the strips against the lid-wall but unlocking the lid can be awkward if the velc is not located appropriately on the strips.

Having focused on a particular outer wall strip, we shall simply call it "the strip". We may assume that the portion of a strip which is adjacent to the lid-wall is square, since the height of the Banj bandaging system and the width of the strip can be adjusted to achieve this. We shall use P, Q, R, and S as names for the points at the corners of this square, going clockwise around the square, with P and Q on the top edge of the strip. The velc on the strip will cover precisely the points in the isosceles right triangle with vertices P, Q, and S. Naturally, the companion velc on the lid-top will mirror this.

To enable the caregiver to grasp the strip and pull it away from the lid-wall to unlock the lid, there will be a little loop of cord attached to the outer wall at point P. The caregiver can use tweezers or a rocker-lock Key which has a hook-shaped lid lifting end to pull the corner at P away from the lid-wall, dragging some of the strip with it. The caregiver should pull that corner slightly away from the lid-wall and generally in the direction of the point R. (Recall that this is a 3-dimensional process.) When the point P gets close to the straight line passing through R which is perpendicular to the local section of the lid-wall, the state of the strip will be similar to what would be achieved by folding the strip along the line from S to Q. The velc on the strip will all have been pulled away from the lid-wall, and this strip will no longer prevent the lid from moving. Note that the symmetry of the velc with respect to a straight line passing through P and R helps this process to go smoothly.

While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A multicomponent bandaging system to address a traumatic insult to human skin comprising:
   a) a base that:
      i) defines a boundary around a wound region of a size sufficient to encompass a wound or other traumatic insult to human skin that merits repeated attention;
      ii) has a generally planar portion adapted to adhere to human skin such that it is not easily dislodged and yet can be removed without causing significant pain; and
      iii) has portions adapted to repeatedly engage with and be disengaged from a lid without adversely affecting the adherence of the base to human skin; and
   b) a generally planar lid that:
      i) is adapted to substantially cover the base; and
      ii) has portions adapted to repeatedly engage with and be disengaged from the base, wherein either the base is essentially planar with no upstanding walls or the lid has depending walls that interact with upstanding walls of the base and wherein:
   c) said interacting portions of the base and the lid interact via a reclosable fastener set in which a portion of one member of the fastener set protrudes into a portion of the other member to cause a frictional adherence; or
   d) the base and the lid each have portions that interact with portions of the other that do not lie in a plane generally parallel to the portion of human skin to which the base is to adhere,
      (a) wherein the portions of the base and the lid that interact with each other are secured to each other using mechanical fasteners that are spaced from each other, and
      (b) wherein the mechanical fasteners comprise sets of two joined lever arms that are permanently affixed to the lid or the base and one of each set has a projection that is adapted to protrude into a recess in the lid or the base to cause a locking action; or
   e) the interacting portions of the base and the lid interact via fasteners carried by either said base interacting portions or said lid interacting portions and adapted to be repeatedly adhered to and removed from a smooth surface and the other interacting portions presents such a smooth surface using nanogrip adhesive technology.

2. The multicomponent bandaging system of claim 1 wherein the base is constructed of a material that can be readily cut with a scissors to fit a particular wound.

3. The multicomponent bandaging system of claim 1 wherein a wound dressing is adhered to a portion of the lid which is to be placed immediately above the traumatic insult.

4. The multicomponent bandaging system of claim 1 wherein the base and the lid each have a portion that interacts with a portion of the other that does not lie in a plane generally parallel to the portion of human skin to which the base is to adhere.

5. The multicomponent bandaging system of claim 4 wherein portions of the base and the lid that interact with each other are substantially perpendicular to the plane encompassing the portion of human skin to which the base is to adhere.

6. The multicomponent bandaging system of claim 4 wherein the interacting lid portion is adapted to fit inside the perimeter defined by the interacting base portion in such a way that the interacting lid portion and the interacting base portion are both accessible from the exterior of the system when in position to interact.

7. The multicomponent bandaging system of claim 4 wherein the interacting portion of the base or the lid is two parallel walls and the interacting portion of the other is a wall adapted to fit between these two parallel walls.

8. The multicomponent bandaging system of claim 7 wherein a recess between the parallel walls and the other wall are both shaped to facilitate the lid easily fitting onto the base.

9. A multicomponent bandaging system comprising:
   a. a base that:
      i. defines a boundary around a wound region of a size sufficient to encompass a wound or other traumatic insult to human skin that merits repeated attention;
      ii. has a generally planar portion adapted to adhere to human skin such that it is not easily dislodged and yet can be removed without causing significant pain; and iii. has portions adapted to repeatedly engage with and be disengaged from a lid without adversely affecting the adherence of the base to human skin; and b. a generally planar lid that:
  i. is adapted to substantially cover the base; and
  ii. has portions adapted to repeatedly engage with and be disengaged from the base, wherein the lid has depending walls that interact with upstanding walls of the base, such that the base and the lid each have portions that interacts with portions of the other that does not lie in a plane generally parallel to the portion of human skin to which the base is to adhere, wherein portions of the base and the lid that interact with each other are secured to each other using mechanical fasteners that are spaced from each other and wherein the mechanical fasteners comprise sets of two joined lever arms that are permanently affixed to a depending or upstanding wall of the lid or the base, respectively, and one of each set has a projection that is adapted to protrude into a recess in the lid or the base to cause a locking action.

10. The multicomponent bandaging system of claim 9 wherein the lever arms that cause engagement lie along the upstanding or depending wall to which the lever arms are affixed when there is engagement and the lever arms that cause disengagement lie along this wall when there is disengagement.

11. The multicomponent bandaging system of claim 9 wherein the lever arms are adapted to be moved into and out of engagement with the recesses with the aid of a key.

12. The multicomponent bandaging system of claim 9 wherein the lever arms carry buttons that facilitate moving them into and out of engagement with the recesses.

13. The multicomponent bandaging system of claim 12 wherein the lever arms that cause disengagement are shorter than the lever arms that cause engagement and consequently carry shorter buttons than the lever arms that cause engagement.

14. A process of addressing a traumatic insult to human skin comprising:
  a. obtaining a multicomponent bandaging system comprising:
    i. a base that:
      1. defines a boundary around a wound region of a size sufficient to encompass a wound or other traumatic insult to human skin that merits repeated attention;
      2. has a generally planar portion adapted to adhere to human skin such that it is not easily dislodged and yet can be removed without causing significant pain; and
      3. has a portion adapted to repeatedly engage with and be disengaged from a lid without adversely affecting the adherence of the base to human skin;
    ii. a generally planar lid that:
      1. is adapted to substantially cover the base; and
      2. has a portion adapted to repeatedly engage with and be disengaged from the base,
    wherein either the base is essentially planar with no upstanding wall or the lid has depending walls that interact with upstanding walls of the base;
      iii. said interacting portions of the base and the lid interact via a reclosable fastener set in which a portion of one member of the fastener set protrudes into a portion of the other member to cause a frictional adherence; or
      iv. the base and the lid each have portions that interact with portions of the other that do not lie in a plane generally parallel to the portion of human skin to which the base is to adhere,
        1. wherein portions of the base and the lid that interact with each other are secured to each other using mechanical fasteners that are spaced from each other, and
        2. wherein the mechanical fasteners comprise sets of two joined lever arms that are permanently affixed to the lid or the base and one of each set has a projection that is adapted to protrude into a recess in the lid or the base to cause a locking action; or
      v. interacting portions of the base and the lid interact via fasteners carried by either said base interacting portions or said lid interacting portions and adapted to be repeatedly adhered to and removed from a smooth surface and the other interacting portions presents such a smooth surface using nanogrip adhesive technology;
  b. adjusting the size of the aperture of the base as necessary to form at least a partial perimeter around said traumatic insult;
  c. adhering the base to a portion of the human skin which surrounds said traumatic insult with an adhesive that is not easily dislodged and yet can be removed without causing significant pain; and
  d. causing a portion of the lid to engage a portion of the base.

15. A two component bandaging system to address a traumatic insult to human skin comprising:
  a. a base that:
    i. defines a boundary around a wound region of a size sufficient to encompass a wound or other traumatic insult to human skin that merits repeated attention;
    ii. has a generally planar portion with an edge adapted to adhere to human skin carrying an adhesive that it is not easily dislodged but can be removed from human skin without causing significant pain and is protected by a readily removable cover sheet; and
    iii. has one or two parallel walls that protrude at an approximately right angle from the outside edge of the base, the number of such walls depending on the number of such walls carried by a lid with only one of the base or the lid having two such walls;
  b. a generally planar lid that:
    substantially covers the base;
    ii. has one or two parallel walls that protrude at an approximately right angle from the edge of the lid, wherein a single wall nests between the two parallel walls when the lid is placed on the base, an outermost wall carries multiple lever arms that can be moved into and out of engagement with recesses in a single wall that nests between the parallel walls to fix the lid to the base; and
    iii. some segments of a planar portion of the lid extend past the edge of base when the lid is placed on the base so as to provide grips.

* * * * *